United States Patent [19]
Beall et al.

[11] Patent Number: 5,877,248
[45] Date of Patent: Mar. 2, 1999

[54] INTERCALATES AND EXFOLIATES FORMED WITH OLIGOMERS AND POLYMERS AND COMPOSITE MATERIALS CONTAINING SAME

[75] Inventors: Gary W. Beall, McHenry; Semeon Tsipursky, Lincolnwood; Anatoliy Sorokin, Wheeling; Anatoliy Goldman, Palatine, all of Ill.

[73] Assignee: Amcol International Corporation, Arlington Heights, Ill.

[21] Appl. No.: 968,408

[22] Filed: Nov. 12, 1997

Related U.S. Application Data

[60] Division of Ser. No. 637,092, May 2, 1996, Pat. No. 5,760,121, which is a continuation-in-part of Ser. No. 488,264, Jun. 7, 1995, Pat. No. 5,552,469, Ser. No. 488,263, Jun. 7, 1995, and Ser. No. 525,416, Sep. 8, 1995, Pat. No. 5,721,306, which is a continuation-in-part of Ser. No. 488,264, Ser. No. 488,263, and Ser. No. 480,080, Jun. 7, 1995, Pat. No. 5,578,672.

[51] Int. Cl.$^6$ .............................. C08J 5/10; C08K 3/34; C08L 39/06
[52] U.S. Cl. .................. 524/450; 524/445; 524/447; 524/448; 524/449
[58] Field of Search ...................... 524/445, 447, 524/448, 450, 449, 503; 523/207, 209, 216

[56] References Cited

U.S. PATENT DOCUMENTS

| | | | |
|---|---|---|---|
| 2,035,546 | 3/1936 | Hamilton | 167/24 |
| 3,419,460 | 12/1968 | Ure | 161/162 |
| 3,419,517 | 12/1968 | Hedrick et al. | 260/37 |
| 3,515,626 | 6/1970 | Duffield | 161/162 |
| 3,773,708 | 11/1973 | Takahashi et al. | 260/41 R |
| 3,795,650 | 3/1974 | Burns | 260/33.4 R |
| 3,912,532 | 10/1975 | Simone | 106/308 N |
| 3,929,678 | 12/1975 | Laughlin et al. | 252/526 |
| 4,125,411 | 11/1978 | Lyons | 106/291 |
| 4,210,572 | 7/1980 | Herman et al. | 260/404 |
| 4,251,576 | 2/1981 | Osborn et al. | 428/331 |
| 4,400,485 | 8/1983 | Mukamal et al. | 524/444 |
| 4,431,755 | 2/1984 | Weber et al. | 523/203 |
| 4,434,075 | 2/1984 | Mardis et al. | 252/315.2 |
| 4,472,538 | 9/1984 | Kamigaito et al. | 523/202 |
| 4,500,670 | 2/1985 | McKinley et al. | 524/445 |
| 4,546,145 | 10/1985 | Kishida et al. | 524/780 |
| 4,600,744 | 7/1986 | Libor et al. | 524/446 |
| 4,613,542 | 9/1986 | Alexander | 428/290 |
| 4,624,982 | 11/1986 | Alexander | 524/446 |
| 4,739,007 | 4/1988 | Okada et al. | 524/789 |
| 4,789,403 | 12/1988 | Rice | 106/417 |
| 4,798,766 | 1/1989 | Rice | 428/404 |
| 4,810,734 | 3/1989 | Kawasumi et al. | 523/216 |
| 4,842,651 | 6/1989 | Ravet et al. | 106/487 |
| 4,849,006 | 7/1989 | Knudson, Jr. | 71/64.11 |
| 4,875,762 | 10/1989 | Kato et al. | 350/357 |
| 4,889,885 | 12/1989 | Usuki et al. | 524/443 |
| 4,894,411 | 1/1990 | Okada et al. | 524/710 |
| 4,920,171 | 4/1990 | Hutton, Jr. et al. | 524/446 |
| 5,032,546 | 7/1991 | Giannelis et al. | 501/3 |
| 5,032,547 | 7/1991 | Giannelis et al. | 501/3 |
| 5,091,462 | 2/1992 | Fukui et al. | 524/504 |
| 5,102,948 | 4/1992 | Deguchi et al. | 524/789 |
| 5,164,440 | 11/1992 | Deguchi et al. | 524/444 |
| 5,164,460 | 11/1992 | Yano et al. | 624/445 |
| 5,204,078 | 4/1993 | Tateyama et al. | 423/331 |
| 5,206,284 | 4/1993 | Fukui et al. | 524/504 |
| 5,229,451 | 7/1993 | Carter et al. | 524/493 |
| 5,248,720 | 9/1993 | Deguchi et al. | 524/444 |
| 5,326,500 | 7/1994 | Friedman et al. | 252/378 |
| 5,340,558 | 8/1994 | Friedman et al. | 423/328.1 |
| 5,385,776 | 1/1995 | Maxfield et al. | 428/297 |
| 5,391,437 | 2/1995 | Miyasaka et al. | 528/425.5 |
| 5,414,042 | 5/1995 | Yasue et al. | 524/789 |
| 5,428,094 | 6/1995 | Tokoh et al. | 524/379 |
| 5,506,046 | 4/1996 | Andersen et al. | 524/446 |
| 5,508,072 | 4/1996 | Andersen et al. | 524/446 |
| 5,514,734 | 5/1996 | Maxfield et al. | 523/204 |
| 5,552,469 | 9/1996 | Beall et al. | 524/445 |
| 5,667,886 | 9/1997 | Gough et al. | 428/331 |

FOREIGN PATENT DOCUMENTS

| | | |
|---|---|---|
| 0 205 281 A3 | 12/1986 | European Pat. Off. |
| 0 335 653 A1 | 10/1989 | European Pat. Off. |
| 0 358 415 A1 | 3/1990 | European Pat. Off. |
| 0 479 031 A1 | 4/1992 | European Pat. Off. |
| 0 548 940 A1 | 6/1993 | European Pat. Off. |
| 0 761 739 A1 | 3/1997 | European Pat. Off. |
| 1 642 122 | 7/1970 | Germany |
| 1 146 668 | 3/1969 | United Kingdom |
| 1 565 362 | 4/1980 | United Kingdom |
| 0 645 181 A2 | 3/1995 | United Kingdom |
| WO 93/04117 | 3/1993 | WIPO |
| WO 93/04118 | 3/1993 | WIPO |
| WO 93/11190 | 6/1993 | WIPO |

OTHER PUBLICATIONS

C. W. Francis, "Adsorption of Polyvinylpyrrolidone on Reference Clay Minerals", Soil Science, vol. 115, No. 1, 1973, pp. 40–54.

(List continued on next page.)

*Primary Examiner*—James J. Seidleck
*Assistant Examiner*—U. K. Rajguru
*Attorney, Agent, or Firm*—Marshall, O'Toole, Gerstein, Murray & Borun

[57] ABSTRACT

Nanocomposites are manufactured by combining a host material, such as an organic solvent or a matrix polymer and exfoliated intercalates formed by contacting a phyllosilicate with a polymer to adsorb or intercalate the polymer between adjacent phyllosilicate platelets. Sufficient polymer is adsorbed between adjacent phyllosilicate platelets to expand the adjacent platelets to a spacing of at least about 5 Å, preferably at least about 10 Å (as measured after water removal), up to about 100 Å and preferably in the range of about 30–40 Å, so that the intercalate easily can be exfoliated, e.g., when mixed with an organic solvent or a polymer melt, to provide a carrier material for drugs and the like, or to provide a matrix polymer/platelet composite (nanocomposite) material—the platelets being exfoliated from the intercalate.

10 Claims, 24 Drawing Sheets

OTHER PUBLICATIONS

A. Usuki, et al., "Synthesis of nylon 6–clay hybrid", J. Mater. Res., vol. 8, No. 5, May 1993, pp. 1179–1184.

Y. Kojima, et al., "Mechanical Properties Of Nylon 6–Clay Hybrid", J. Mater. Res., vol. 8, No. 5, May 1993, pp. 1185–1189.

K. Suzuki, et al., "Preparation Of Delaminated Clay Having A Narrow Micropore Distribution In the Presence Of Hydroxyaluminum Cations And Polyvinyl Alcohol", Clays and Clay Minerals, vol. 36, No. 2, 1988, pp. 147–152.

R. Levy, et al., "Interlayer Adsorption of Polyvinylpyrrolidone On Montmorillonite", Journal of Colloid and Interface Science, vol. 50, No. 3, Mar. 1975, pp. 442–450.

D.J. Greenland, "Adsorption Of Polyvinyl Alcohols By Montmorillonite", Journal of Colloid Science, 18, (1963) pp. 647–664.

R.A. Vaia, et al., "Synthesis and Properties of Two–Dimensional Nanostructures by Direct Intercalation of Polymer Melts in Layered Silicates", Chem. Mater. 1993, 5, pp. 1694–1696.

R.A. Vaia, et al., "New Polymer Electrolyte Nanocomposites: Melt Intercalation of Poly(ethylene oxide) in Mica–Type Silicates", Advanced Materials 1995, 7, No. 2, pp. 154–156.

A. Akelah, et al., "Synthesis and Characterization of Epoxyphilic montmorillonites", Clay Minerals (1994) 29, pp. 169–178.

C.E. Clapp, et al., "Adsorption Studies Of A Dextran On Montmorillonite", Trans. 9th Int. Cong. Soil Sci., 1968, vol. 1, pp. 627–634.

H.G.G. Dekking, "Preparation And Properties Of Some Polymer–Clay Compounds", Clays and Clay Minerals, 1964, 12, pp. 603–616.

A. Usuki, et al., "Characterization and Properties of Nylon 6 — Clay Hybrid", (source and date unknown), pp. 651–652.

G.W. Brindley, et al., "Preparation And Solvatio Properties Of Some Variable Charge Montmorillonites", Clays and Clay Minerals, 1971, vol. 18, pp. 399–404.

A. Okada, et al., "A Solid State NMR Study On Crystalline Forms Of Nylon 6", Journal of Applied Polymer Science, (1989), vol. 37, pp. 1363–1371.

A. Usuki, et al., Swelling Behavior Of Montmorillonite Cation Exchanged For ω–Amino Acids By ε–Caprolactam, J. Mater. Res., vol. 8, No. 5, May 1993, pp. 1174–1178.

Y. Kojima, et al., "One–Pot Synthesis Of Nylon 6–Clay Hybrid", Journal of Polymer Science: Part A: Polymer Chemistry, vol. 31, (1993), pp. 1755–1758.

Y. Kojima, et al., "Fine Structure Of Nylon–6–Clay Hybrid", Journal of Polymer Science: Part B: Polymer Physics, vol. 32 (1994), pp. 625–630.

B.K.G. Theng, "Clay–Polymer interactions: Sumary And Perspectives", Clays and Clay Minerals, vol. 30, No. 1 (1982) pp. 1–9.

Sugahara, et al., "Clay–Organic Nano–Composite; Preparation of a Kaolinite–Poly(vinylpyrrolidone) Intercalation Compound", *Journal of the Ceramic Society of Japan*, International Edition, vol. 100, No. 4, Apr. 1, 1992, pp. 420–423.

Ogawa, et al., "Preparation Of Montmorillonite–Polyacrylamide Intercalation Compounds And The Water Absorbing Property", *Clay Science*, vol. 7, 1989 Tokyo, Japan, pp. 243–251.

Wu, et al., "Structural, thermal, and electrical characterization of layered nanocomposites derived from sodium–montmorillonite and polyethers", *Chemical Abstracts*, vol. 119, No. 4, Jul. 26, 1993 Columbus, Ohio, US, Abstract No. 31017r.

Bujdak, et al., "The reaction of montmorillonite with octadecylamine in solid and melted state", Chemical Abstracts, vol. 118, No. 26, Abstract No. 257609b, p. 166 (28 Jun. 1993), Columbus, Ohio (US).

Yano, et al., "Synthesis And Properties Of Polyimide–Clay Hybrid", Polymer Preprints, ACS, Apr. 1991, pp. 65–66.

Giannelis, et al., "Synthesis And Processing Of Ceramics: Scientific Issues", Materials Research Society Symposium Proceedings, vol. 249 (1992), pp. 547–558.

Sanchez Camazano, M. et al., "Factors influencing interactions of organophosphorus pesticides with montmorillonite", *Chemical Abstracts*, vol. 98, No. 19, 9 May 1983, Columbus, Ohio, US, Abstract No. 156367.

T. Lan et al., "Clay–Epoxy Nanocomposites:Relationships Between Reinforcement Properties And The Extent Of Clay Layer Exfoliation", Polym. Mater. Sci. Eng., vol. 73, 296–297 (1995).

INTERCALATES AND EXFOLIATES FORMED WITH OLIGOMERS AND POLYMERS AND COMPOSITE MATERIALS CONTAINING SAME

CROSS-REFERENCE TO RELATED APPLICATIONS

This application is a divisional of U.S. application Ser. No. 08/637,092 filed May 2, 1996, now U.S. Pat. No. 5,760,121 which is a continuation-in-part of U.S. patent application Ser. Nos. 08/525,416 filed Sep. 8, 1995, now U.S. Pat. No. 5,721,306; Ser. No. 08/488,264 filed Jun. 7, 1995, now U.S. Pat. No. 5,552,469 and Ser. No. 08/488,263 filed Jun. 7, 1995. U.S. patent application Ser. No. 08/525,416 a continuation-in-part of U.S. patent application Ser. Nos. 08/488,264 filed Jun. 7, 1995 now U.S. Pat. No. 5,552,469; Ser. No. 08/488,263 filed Jun. 7, 1995, and Ser. No. 08/480,080 filed Jun. 7, 1995, now U.S. Pat. No. 5,578,672.

FIELD OF THE INVENTION

The present invention is directed to intercalated layered materials, and exfoliates thereof, manufactured by sorption (adsorption and/or absorption) of one or more oligomers or polymers between planar layers of a swellable layered material, such as a phyllosilicate or other layered material, to expand the interlayer spacing of adjacent layers to at least about 5 Å. More particularly, the present invention is directed to intercalates having at least two layers of oligomer and/or polymer molecules sorbed on the internal surfaces of adjacent layers of the planar platelets of a layered material, such as a phyllosilicate, preferably a smectite clay, to expand the interlayer spacing to at least about 5 Angstroms, preferably at least about 10 Angstroms, more preferably to at least about 20 Angstroms, and most preferably to at least about 30–45 Angstroms, up to about 100 Å, or disappearance of periodicity. The resulting intercalates are neither entirely organophilic nor entirely hydrophilic, but a combination of the two, and easily can be exfoliated for or during admixture with a thermoplastic or thermosetting matrix polymer melt, preferably a thermoplastic matrix polymer, to improve one or more properties of the matrix polymer. The resulting matrix polymer/platelet composite materials are useful wherever polymer/filler composite materials are used, for example, as external body parts for the automotive industry; heat-resistant polymeric automotive parts in contact with an engine block; tire cord for radial tires; food wrap having improved gas impermeability; electrical components; food grade drink containers; and any other use where it is desired to alter one or more physical properties of a matrix polymer, such as elasticity and temperature characteristics, e.g., glass transition temperature and high temperature resistance.

BACKGROUND OF THE INVENTION AND PRIOR ART

It is well known that phyllosilicates, such as smectite clays, e.g., sodium montmorillonite and calcium montmorillonite, can be treated with organic molecules, such as organic ammonium ions, to intercalate the organic molecules between adjacent, planar silicate layers, thereby substantially increasing the interlayer (interlaminar) spacing between the adjacent silicate layers. The thus-treated, intercalated phyllosilicates then can be exfoliated, e.g., the silicate layers are separated, e.g., mechanically, by high shear mixing. The individual silicate layers, when admixed with a matrix polymer, before, after or during the polymerization of the matrix polymer, e.g., a polyamide—see U.S. Pat. Nos. 4,739,007; 4,810,734; and 5,385,776—have been found to substantially improve one or more properties of the polymer, such as mechanical strength and/or high temperature characteristics.

Exemplary of such prior art composites, also called "nanocomposites", are disclosed in published PCT disclosure of Allied Signal, Inc. WO 93/04118 and U.S. Pat. No. 5,385,776, disclosing the admixture of individual platelet particles derived from intercalated layered silicate materials, with a polymer to form a polymer matrix having one or more properties of the matrix polymer improved by the addition of the exfoliated intercalate. As disclosed in WO 93/04118, the intercalate is formed (the interlayer spacing between adjacent silicate platelets is increased) by adsorption of a silane coupling agent or an onium cation, such as a quaternary ammonium compound, having a reactive group which is compatible with the matrix polymer. Such quaternary ammonium cations are well known to convert a highly hydrophilic clay, such as sodium or calcium montmorillonite, into an organophilic clay capable of sorbing organic molecules. A publication that discloses direct intercalation (without solvent) of polystyrene and poly (ethylene oxide) in organically modified silicates is *Synthesis and Properties of Two-Dimensional Nanostructures by Direct Intercalation of Polymer Melts in Layered Silicates*, Richard A. Vaia, et al., *Chem. Mater.*, 5:1694–1696(1993). Also as disclosed in Adv. Materials, 7, No. 2: (1985), pp, 154–156, *New Polymer Electrolyte Nanocomposites: Melt Intercalation of Poly(Ethylene Oxide) in Mica-Type Silicates,* Richard A. Vaia, et al., poly(ethylene oxide) can be intercalated directly into Na-montmorillonite and Li-montmorillonite by heating to 80° C. for 2–6 hours to achieve a d-spacing of 17.7 Å. The intercalation is accompanied by displacing water molecules, disposed between the clay platelets with polymer molecules. Apparently, however, the intercalated material could not be exfoliated and was tested in pellet form. It was quite surprising to one of the authors of these articles that exfoliated material could be manufactured in accordance with the present invention.

Previous attempts have been made to intercalate polyvinylpyrrolidone (PVP), polyvinyl alcohol (PVA) and poly (ethylene oxide) (PEO) between montmorillonite clay platelets with little success. As described in Levy, et al., *Interlayer Adsorption of Polyvinylpyrrolidone on Montmorillonite,* Journal of Colloid and Interface Science, Vol. 50, No. 3, March 1975, pages 442–450, attempts were made to sorb PVP (40,000 average M.W.) between monoionic montmorillonite clay platelets (Na, K, Ca and Mg) by successive washes with absolute ethanol, and then attempting to sorb the PVP by contact with 1% PVP/ethanol/water solutions, with varying amounts of water, via replacing the ethanol solvent molecules that were sorbed in washing (to expand the platelets to about 17.7 Å). Only the sodium montmorillonite had expanded beyond a 20 Å basal spacing (e.g., 26 Å and 32 Å), at $5^+$% $H_2O$, after contact with the PVP/ethanol/$H_2O$ solution. It was concluded that the ethanol was needed to initially increase the basal spacing for later sorption of PVP, and that water did not directly affect the sorption of PVP between the clay platelets (Table II, page 445), except for sodium montmorillonite. The sorption was time consuming and difficult and met with little success.

Further, as described in Greenland, *Adsorption of Polyvinyl Alcohols by Montmorillonite,* Journal of Colloid Sciences, Vol. 18, pages 647–664 (1963), polyvinyl alcohols containing 12% residual acetyl groups could increase the basal spacing by only about 10 Å due to the sorbed polyvinyl alcohol (PVOH). As the concentration of polymer in the intercalant polymer-containing solution was increased from 0.25% to 4%, the amount of polymer sorbed was substantially reduced, indicating that sorption might only be effective at polymer concentrations in the intercalant polymer-containing composition on the order of 1% by weight polymer, or less. Such a dilute process for intercalation of polymer into layered materials would be exceptionally costly in drying the intercalated layered materials for separation of intercalate from the polymer carrier, e.g., water, and, therefore, apparently no further work was accomplished toward commercialization.

In accordance with one embodiment of the present invention, intercalates are prepared by contacting a phyllosilicate with a PVP polymer, preferably essentially alcohol-free, or a PVA intercalant polymer composition, wherein the PVA preferably contains 5% or less residual acetyl groups, more preferably fully hydrolyzed, containing 1% or less acetyl groups.

In accordance with an important feature of the present invention, best results are achieved using an oligomer (herein defined as a pre-polymer having 2 to about 15 recurring monomeric units, which can be the same or different) or polymer (herein defined as having more than about 15 recurring monomeric units, which can be the same or different) composition for intercalation having at least about 2%, preferably at least about 5% by weight intercalant oligomer or intercalant polymer concentration, more preferably about 50% to about 80% by weight oligomer and/or polymer, based on the weight of oligomer and/or polymer and carrier (e.g., water and/or other solvent for the intercalant oligomer or intercalant polymer) to achieve better sorption of the intercalant polymers between phyllosilicate platelets and so that less drying is required after intercalation. The oligomer or polymer sorbed between silicate platelets that causes separation or added spacing between adjacent silicate platelets and, for simplicity of description, both the oligomers and polymers are hereinafter called the "intercalant" or "intercalant polymer" or "polymer intercalant". In this manner, water-soluble or water-insoluble oligomers or polymers will be sorbed sufficiently to increase the interlayer spacing of the phyllosilicate in the range of about 5 Å to about 100 Å, for easier and more complete exfoliation, in a commercially viable process, regardless of the particular phyllosilicate or intercalant polymer.

In accordance with an important feature of the present invention, best results are achieved using a water-soluble or water-insoluble oligomer (herein defined as a pre-polymer having 2 to about 15 recurring monomeric units, which can be the same or different) or polymer (herein defined as having more than about 15 recurring monomeric units, which can be the same or different) composition for intercalation having at least about 2%, preferably at least about 5% by weight, more preferably at least about 10% by weight intercalant oligomer or intercalant polymer concentration, most preferably about 30% to about 80% by weight oligomer and/or polymer, based on the weight of oligomer and/or polymer and carrier (e.g., water with or without another solvent for the intercalant oligomer or intercalant polymer) to achieve better sorption of the intercalant polymers between phyllosilicate platelets. Regardless of the concentration of polymer in liquid solvent of the intercalating composition, the intercalating composition should have a polymer:layered material ratio of at least 1:20, preferably at least 1:10, more preferably at least 1:5, and most preferably about 1:4 to achieve efficient intercalation of the polymer between adjacent platelets of the layered material. The oligomer or polymer sorbed between and permanently bonded to the silicate platelets causes separation or added spacing between adjacent silicate platelets and, for simplicity of description, both the oligomers and polymers are hereinafter called the "intercalant" or "intercalant polymer" or "polymer intercalant". In this manner, the oligomers or polymers will be sorbed sufficiently to increase the interlayer spacing of the phyllosilicate in the range of about 5 Å to about 100 Å, preferably at least about 10 Å, for easier and more complete exfoliation, in a commercially viable process, regardless of the particular phyllosilicate or intercalant polymer.

A phyllosilicate, such as a smectite clay, can be intercalated sufficiently for subsequent exfoliation by sorption of polymers or oligomers that have carbonyl, hydroxyl, carboxyl, amine, amide, ether, ester, sulfate, sulfonate, sulfinate, sulfamate, phosphate, phosphonate, phosphinate functionalities, or aromatic rings to provide metal cation chelate-type bonding between two functional groups of one or two intercalant polymer molecules and the metal cations bonded to the inner surfaces of the phyllosilicate platelets. Sorption and metal cation electrostatic attraction or bonding of a platelet metal cation between two oxygen or nitrogen atoms of the molecules; or the electrostatic bonding between the interlayer cations in hexagonal or pseudohexagonal rings of the smectite layers and an intercalant polymer aromatic ring structure increases the interlayer spacing between adjacent silicate platelets or other layered material to at least about 5 Å, preferably at least about 10 Å, and more preferably at least about 20 Å, and most preferably in the range of about 30 Å to about 45 Å. Such intercalated phyllosilicates easily can be exfoliated into individual phyllosilicate platelets.

Depending upon the conditions that the composition is subjected to during intercalation and exfoliation, particularly temperature; pH; and amount of water contained in the intercalating composition, the intercalate and/or exfoliate/carrier composition can be formed to any desired viscosity, e.g., at least about 100 centipoises, preferably at least about 500–1000 centipoises, whether or not gelled, and particularly to extremely high viscosities of about 5,000 to about 5,000,000 centipoises. The compositions are thixotropic so that shearing will lower viscosity for easier delivery, and then by reducing shear or eliminating shear, the compositions will increase in viscosity. The intercalant polymer intercalates between the spaces of adjacent platelets of the layered material for easy exfoliation, and complexes with the metal cations on the platelet surfaces where the polymer remains after the intercalate, or exfoliate thereof, is combined with the carrier/solvent or added to a polymer melt. It is theorized that the polymer coating on the surfaces of the clay platelets is ionically complexed with interlayer cations and participates (aids) in the viscosification and thixotropy of the carrier/solvent composition and adds significant strength, vapor impermeability and temperature characteristics to a matrix polymer. However, other forms of bonding such as hydrogen bonding or Van Der Waals forces or molecular complexing also may be responsible for the adherence of the polymer to the surfaces of the layered material, either entirely, or in part.

DEFINITIONS

Whenever used in this Specification, the terms set forth shall have the following meanings:

"Layered Material" shall mean an inorganic material, such as a smectite clay mineral, that is in the form of a plurality of adjacent, bound layers and has a thickness, for each layer, of about 3 Å to about 50 Å, preferably about 10 Å.

"Platelets" shall mean individual layers of the Layered Material.

"Intercalate" or "Intercalated" shall mean a Layered Material that includes oligomer and/or polymer molecules disposed between adjacent platelets of the Layered Material to increase the interlayer spacing between the adjacent platelets to at least about 5 Å, preferably at least about 10 Å.

"Intercalation" shall mean a process for forming an Intercalate.

"Intercalant Polymer" or "Intercalant" shall mean an oligomer or polymer that is sorbed between Platelets of the Layered Material and complexes with the platelet surfaces to form an Intercalate.

"Intercalating Carrier" shall mean a carrier comprising water with or without an organic solvent used together with an Intercalant Polymer to form an Intercalating Composition capable of achieving Intercalation of the Layered Material.

"Intercalating Composition" shall mean a composition comprising an Intercalant Polymer, an Intercalating Carrier for the Intercalant Polymer, and a Layered Material.

"Exfoliate" or "Exfoliated" shall mean individual platelets of an Intercalated Layered Material so that adjacent platelets of the Intercalated Layered Material can be dispersed individually throughout a matrix polymer; or throughout a carrier material, such as water, an alcohol or glycol, or any other organic solvent.

"Exfoliation" shall mean a process for forming an Exfoliate from an Intercalate.

"Nanocomposite" shall mean an oligomer, is polymer or copolymer having dispersed therein a plurality of individual platelets obtained from an Exfoliated, Intercalated Layered Material.

"Matrix Polymer" shall mean a thermoplastic or thermosetting polymer in which the Intercalate and/or Exfoliate is dispersed to form a Nanocomposite.

SUMMARY OF THE INVENTION

In brief, the present invention is directed to intercalates formed by contacting a layered phyllosilicate with an oligomer and/or polymer to sorb or intercalate the intercalant polymer or mixtures of intercalant polymers between adjacent phyllosilicate platelets. Sufficient intercalant polymer is sorbed between adjacent phyllosilicate platelets to expand the spacing between adjacent platelets (interlayer spacing) to a distance of at least about 5 Å, preferably to at least about 10 Å (as measured after water removal) and more preferably in the range of about 30–45 Å, so that the intercalate easily can be exfoliated, sometimes naturally, without shearing being necessary. At times, the intercalate requires shearing that easily can be accomplished, e.g., when mixing the intercalate with a polymer melt, to provide a matrix polymer/platelet composite material or nanocomposite—the platelets being obtained by exfoliation of the intercalated phyllosilicate.

The intercalant polymer should have an affinity for the phyllosilicate so that it is sorbed between, and is maintained associated with the silicate platelets in the interlayer spaces, and after exfoliation. In accordance with a preferred embodiment of the present invention, the intercalant polymer should include an aromatic ring and/or have a functionality selected from the group consisting of a carbonyl; carboxyl; hydroxyl; amine; amide; ether; ester; sulfate; sulfonate; sulfinate; sulfamate; phosphate; phosphonate; or phosphinate structure to be sufficiently bound to an inner surface of the phyllosilicate. It is hereby theorized that polymer binding to the platelet surfaces is by metal cation electrostatic bonding or complexing, e.g., chelation, of the metal cations of the phyllosilicate sharing electrons with two carbonyl, two carboxyl, two hydroxyl, two oxygen, two amine, two $SO_x$, two $PO_x$ (wherein x=2, 3, or 4) and/or two amide functionalities of one intercalant polymer molecule, or of two adjacent intercalant polymer molecules to an inner surface of the phyllosilicate platelets. Such intercalant polymers have sufficient affinity for the phyllosilicate platelets to provide sufficient interlayer spacing for exfoliation, e.g., about 5 Å–100 Å, preferably about 10 Å–50 Å, and to maintain attachment to the surfaces of the platelets, without the need for coupling agents or spacing agents, such as the onium ion or silane coupling agents disclosed in the above-mentioned prior art.

Sorption of the intercalant polymer should be sufficient to achieve expansion of adjacent platelets of the layered material (when measured dry—having a maximum of about 5 by weight water) to an interlayer spacing of at least about 5 Å, preferably a spacing of at least about 10 Å, more preferably a spacing of at least about 20 Å, and most preferably a spacing of about 30–45 Å. To achieve intercalates that can be exfoliated easily using the preferred water-soluble polymer intercalants disclosed herein, such as polyvinylpyrrolidone, polyvinyl alcohol, and mixtures thereof, the weight ratio of intercalant polymer to layered material, preferably a water-swellable smectite clay such as sodium bentonite, in the intercalating composition contacting the phyllosilicate should be at least about 1:20, preferably at least about 1:12 to 1:10, more preferably at least about 1:5, and most preferably about 1:5 to about 1:3. It is preferred that the concentration of polymer in the intercalating composition, based on the total weight of polymer plus intercalant carrier (water plus any organic liquid solvent) in the intercalating composition is at least about 15% by weight, more preferably at least about 20% by weight polymer, for example about 20%–30% to about 90% by weight polymer, based on the weight of polymer plus intercalant carrier (water plus any organic solvent) in the intercalant composition during intercalation.

It has been found that the intercalates of the present invention are increased in interlayer spacing step-wise. If the phyllosilicate is contacted with an intercalant polymer-containing composition containing less than about 16% by weight polymer, e.g., 10% to about 15% by weight polymer, based on the dry weight of the phyllosilicate, a monolayer width of polymer is sorbed (intercalated) between the adjacent platelets of the layered material. A monolayer of polymer intercalated between platelets increases the interlayer spacing to about 5 Å to less than 10 Å. When the amount of intercalant polymer is in the range of about 16% to less than about 35% by weight, based on the weight of the dry layered material, the intercalant polymer is sorbed in a bilayer, thereby increasing the interlayer spacing to about 10 Å to about 16 Å, as shown in FIGS. 1 and 2. At an intercalant polymer loading in the intercalant-containing composition of about 35% to less than about 55% intercalant polymer, based on the dry weight of the layered material contacted, the interlayer spacing is increased to about 20 Å to about 25 Å, corresponding to three layers of intercalant polymer sorbed between adjacent platelets of the layered material, as shown in FIGS. 1 and 2. At an intercalant polymer loading of about 55% to about 80% intercalant polymer, based on the dry weight of the layered material dissolved or dispersed in the intercalant polymer-containing composition, the interlayer spacing will be increased to about 30 Å to about 35 Å, corresponding to 4 and 5 layers of intercalant polymer sorbed (intercalated) between adjacent platelets of the layered material, as shown in FIGS. 1 and 2.

Such interlayer spacings have never been achieved by direct intercalation of an oligomer or polymer molecule, without prior sorption of a swelling agent, such as an onium or silane coupling agent, and provides easier and more complete exfoliation for or during incorporation of the platelets into a thermoplastic or thermosetting matrix polymer. Such intercalates are especially useful in admixture with matrix thermoplastic or thermosetting polymers in the manufacture of polymeric articles from the polymer/platelet composite materials; and for admixture of the intercalates and exfoliated intercalates with polar solvents in modifying rheology, e.g., of cosmetics, oil-well drilling fluids, paints, lubricants, especially food grade lubricants in the manufacture of oil and grease, and the like.

Once exfoliated, the platelets of the intercalate are predominantly completely separated into individual platelets having intercalant polymer molecules complexed with the platelet surfaces, and the originally adjacent platelets no longer are retained in a parallel, spaced disposition, but are free to move as predominantly individual, polymer coated (continuously or discontinuously) platelets throughout a carrier or throughout a matrix polymer melt to act similar to a nanoscale filler material for the matrix polymer. The predominantly individual phyllosilicate platelets, having their platelet surfaces complexed with polymer molecules, are randomly, homogeneously and uniformly dispersed throughout a carrier, such as water or an organic liquid, or throughout a polymer melt. Once a matrix polymer/platelet composite material is set and hardened into a desired shape, the predominantly individual phyllosilicate platelets are permanently fixed in position and are randomly, homogeneously and uniformly dispersed, predominantly as individual platelets, throughout the matrix polymer/platelet composite material.

As recognized, the thickness of the exfoliated, individual platelets (about 10 Å) is relatively small compared to the size of the flat opposite platelet faces. The platelets have an aspect ratio in the range of about 200 to about 2,000. Dispersing such finely divided platelet particles into a polymer melt provides a very large area of contact between polymer and platelet particles, for a given volume of particles in the composite, and a high degree of platelet homogeneity in the composite material. Platelet particles of high strength and modulus, dispersed at sub-micron size (nanoscale), impart greater mechanical reinforcement and a higher glass transition temperature (Tg) to the polymer matrix than do comparable loadings of conventional reinforcing fillers of micron size, and can impart lower permeability to matrix polymers than do comparable loadings of conventional fillers.

While the nanocomposites disclosed in WO 93/04118 require a swelling/compatibilizing agent, such as a silane coupling agent, or a quaternary ammonium molecule, that has distinct bonding interactions with both the polymer and the platelet particle to achieve improved properties in the polymer, the polymer intercalants used to form the intercalates and exfoliates in accordance with the present invention need not have any (but can include) reactivity with the matrix polymer in which the inventive intercalates and exfoliates are dispersed, while improving one or more properties of the matrix polymer.

DETAILED DESCRIPTION OF THE PREFERRED EMBODIMENTS

Figure 1:
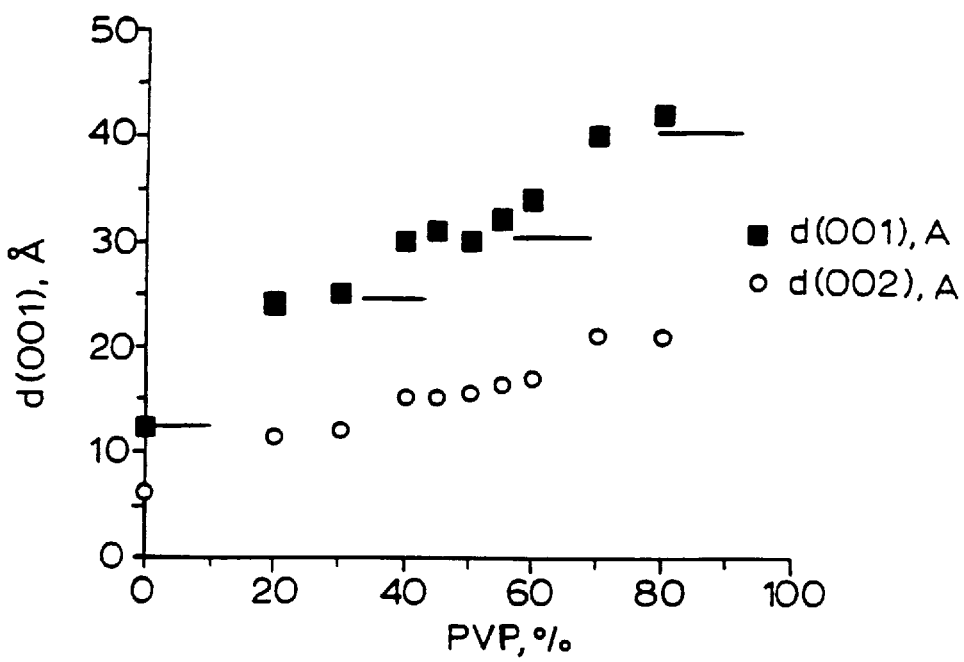
FIG. 1 is a graph plotting interlayer space for polyvinylpyrrolidone (PVP):smectite clay complexes (intercalates) showing d(001) and d(002) spacing, in Angstroms, between smectite clay platelets versus percentage of PVP sorbed, based on the dry weight of the smectite clay.

To form the intercalated materials of the present invention, the phyllosilicate should be swelled or intercalated by sorption of a water-soluble oligomer or polymer that includes an aromatic ring and/or a functionality selected from the group consisting of carbonyl; carboxyl; hydroxyl; amine; amide; ether; ester; sulfate; sulfonate; sulfinate; sulfamate; phosphate; phosphonate; or phosphinate; or combinations thereof. In accordance with a preferred embodiment of the present invention, the phyllosilicate should include at least 4% by weight water, up to about 5000% water, based on the dry weight of the phyllosilicate, preferably about 7% to about 100% water, more preferably about 25% to about 50% by weight water, prior to or during contact with the intercalant polymer to achieve sufficient intercalation for exfoliation. Preferably, the phyllosilicate should include at least about 4% by weight water before contact with the intercalating carrier for efficient intercalation. The amount of intercalant polymer in contact with the phyllosilicate from the intercalating composition, for efficient exfoliation, should provide an intercalant polymer/phyllosilicate weight ratio (based on the dry weight of the phyllosilicate) of at least about 1:20, preferably at least about 3.2:20, and more preferably about 4–14:20, to provide efficient sorption and complexing (intercalation) of the polymer between the platelets of the layered material, e.g., phyllosilicate, (preferably about 16% to about 70% by weight intercalant polymer, based on the dry weight of the layered silicate material).

The polymer intercalants are introduced in the form of a solid or liquid composition (neat or aqueous solution or dispersion, and/or with an organic solvent, e.g., hydroalcoholic) having an intercalant polymer concentration of at least about 2%, preferably at least about 5% by weight polymer, more preferably at least about 50% to about 100% by weight intercalant polymer in the polymer/carrier composition contacting the layered material for intercalant polymer sorption. The polymer can be water-soluble, water-insoluble or partially water-soluble and can be added as a liquid or solid with the addition to the layered material/polymer blend of at least about 20% water, e.g., about 20% to about 80% water, preferably at least about 30% water to about 5000% water and/or other solvent for the intercalant polymer, based on the dry weight of layered material plus polymer, preferably about 30% to about 50% water or other solvent, so that less water or solvent is sorbed by the intercalate, thereby necessitating less drying energy after intercalation. The intercalant polymer may be introduced into the spaces between every layer, nearly every layer, or at least a predominance of the layers of the layered material such that the subsequently exfoliated platelet particles are preferably, predominantly less than about 5 layers in thickness; more preferably, predominantly about 1 or 2 layers in thickness; and most preferably, predominantly single platelets.

Any swellable layered material that sufficiently sorbs the intercalant polymer to increase the interlayer spacing between adjacent phyllosilicate platelets to at least about 5 Å, preferably at least about 10 Å (when the phyllosilicate is measured dry—having a maximum of about 5% by weight water) may be used in the practice of this invention. Useful swellable layered materials include phyllosilicates, such as smectite clay minerals, e.g., montmorillonite, particularly sodium montmorillonite; magnesium montmorillonite and/or calcium montmorillonite; nontronite; beidellite; volkonskoite; hectorite; saponite; sauconite; sobockite; stevensite;, svinfordite; vermiculite; and the like. Other useful layered materials include micaceous minerals, such as illite and mixed layered illite/smectite minerals, such as ledikite and admixtures of illites with the clay minerals named above.

Other layered materials having little or no charge on the layers may be useful in this invention provided they can be intercalated with the intercalant polymers to expand their interlayer spacing to at least about 5 Å, preferably to at least about 10 Å. Preferred swellable layered materials are phyllosilicates of the 2:1 type having a negative charge on the layers ranging from about 0.15 to about 0.9 charges per formula unit and a commensurate number of exchangeable metal cations in the interlayer spaces. Most preferred layered materials are smectite clay minerals such as montmorillonite, nontronite, beidellite, volkonskoite, hectorite, saponite, sauconite, sobockite, stevensite, and svinfordite.

As used herein the "interlayer spacing" refers to the distance between the internal faces of the adjacent dry layers as they are assembled in the layered material before any delamination (exfoliation) takes place. The interlayer spacing is measured when the layered material is "air dry", e.g., contains about 3–10% by weight water, preferably about 3–6% by weight water, based on the dry weight of the layered material. The preferred clay materials generally include interlayer cations such as $Na^+$, $Ca^{+2}$, $K^+$, $Mg^{+2}$, $NH_4^+$ and the like, including mixtures thereof.

The amount of intercalant polymer intercalated into the swellable layered materials useful in this invention, in order that the intercalated layered material may be exfoliated or delaminated into individual platelets, may vary substantially between about 10% and about 80%, based on the dry weight of the layered silicate material. In the preferred embodiments of the invention, amounts of polymer intercalants employed, with respect to the dry weight of layered material being intercalated, will preferably range from about 8 grams of intercalant polymer/100 grams of layered material (dry basis), more preferably at least about 10 grams of polymer/100 grams of layered material, to about 80–90 grams intercalant polymer/100 grams of layered material (dry basis). More preferred amounts are from about 20 grams intercalant polymer/100 grams of layered material to about 60 grams intercalant polymer/100 grams of layered material (dry basis).

The polymer intercalants are introduced into (sorbed within) the interlayer spaces of the layered material in one of two ways. In a preferred method of intercalating, the layered material is intimately mixed, e.g., by extrusion, with a concentrated intercalant polymer or intercalant polymer/water solution, or intercalant polymer/organic solvent, e.g., ethanol solution. To achieve the best intercalation for exfoliation, the layered material/intercalant polymer blend contains at least about 8% by weight intercalant polymer, preferably at least about 10% by weight intercalant polymer, based on the dry weight of the layered material. The intercalating carrier (preferably water, with or without an organic solvent, e.g., ethanol) can be added by first solubilizing or dispersing the polymer in the carrier; or the dry polymer and relatively dry phyllosilicate (preferably containing at least about 4% by weight water) can be blended and the intercalating carrier added to the blend, or to the phyllosilicate prior to adding the dry intercalant polymer. In every case, it has been found that surprising sorption and complexing of intercalant polymer between platelets is achieved at relatively low loadings of intercalating carrier, especially $H_2O$, e.g., about 4% by weight water, based on the dry weight of the phyllosilicate.

When intercalating the phyllosilicate in slurry form (e.g., 900 pounds water, 100 pounds phyllosilicate, 25 pounds polymer) the amount of water can vary from a preferred minimum of at least about 30% by weight water, with no upper limit to the amount of water in the intercalating composition (the phyllosilicate intercalate is easily separated from the intercalating composition).

Alternatively, the intercalating carrier, e.g., water, with or without an organic solvent, can be added directly to the phyllosilicate prior to adding the intercalant polymer, either dry or in solution. Sorption of the polymer intercalant molecules may be performed by exposing the layered material to dry or liquid polymer intercalant compositions containing at least about 2% by weight, preferably at least about 5% by weight intercalant polymer, more preferably at least about 50% polymer, based on the dry weight of the layered material. Sorption may be aided by exposure of the intercalating composition to heat, pressure, ultrasonic cavitation, or microwaves.

In accordance with another method of intercalating the intercalant polymer between the platelets of the layered material and exfoliating the intercalate, the layered material, containing at least about 4% by weight water, preferably about 10% to about 15% by weight water, is blended with a solubilized intercalant polymer (in a water or organic solvent carrier) in a ratio sufficient to provide at least about 8% by weight, preferably at least about 10% by weight intercalant polymer, based on the dry weight of the layered material. The blend then preferably is extruded for faster intercalation. Further, the blend can be heated to at least the melt temperature of the intercalant polymer, and preferably at least about 40°–50° C. above the intercalant polymer melt temperature for faster intercalation.

In accordance with one important embodiment of the present invention, one or more polymerizable monomers can be intercalated between the platelets of the layered material, or simply admixed with the exfoliated layered material, and the polymerizable monomer(s) are polymerized while intercalated between platelets, or while in contact with the intercalate or exfoliated intercalate. The polymerizable monomer(s) can be, for example, a mixture of an acrylic acid and a polymerization initiator for the acrylic acid to produce water-soluble polyacrylic acid or polyacrylate; or a cross-linking agent can be added to produce a water-insoluble polymer; or the monomer(s) can be any of the polymerizable organic liquids, that polymerize to form a polymer, such as the water-soluble polymers disclosed in U.S. Pat. No. 4,251,576, hereby incorporated by reference.

Suitable water-insoluble polymerizable monomer(s) can be, for example, a mixture of a diamine and a dicarboxylic acid suitable for reaction to produce a polyamide, e.g., nylon; or the monomer(s) can be any of the polymerizable organic liquids, that polymerize to form a water-insoluble polymer, disclosed in U.S. Pat. No. 4,251,576, hereby incorporated by reference.

The preferred polymer intercalants are water-soluble, such as polyvinylpyrrolidone (PVP) having a monomeric structure (I) as follows:

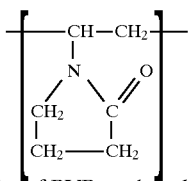
(I)

The water-solubility of PVP can be adjusted according to (1) the degree of hydrolysis of the polyvinylpyrrolidone, and (2) by forming a metal salt of PVP, such as sodium or potassium. PVP can be hydrolyzed to the structure (II):

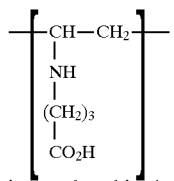
(II)

and the PVP can be intercalated in the salt form, e.g., sodium or potassium polyvinylpyrrolidone. Preferred PVP intercalants, and the following PVP derivatives, should have a weight average molecular weight in the range of about 100 to about 100,000 or more, more preferably about 1,000 to about 40,000.

Other suitable water-soluble vinyl polymers include poly(vinyl alcohol)

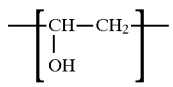

The polyvinyl alcohols function best when they are essentially fully hydrolyzed, e.g., 5% or less acetyl groups, preferably 1% or less residual acetyl groups. The lower molecular weight PVA's function best, e.g., a weight average molecular weight of about 2,000 to about 10,000, but higher molecular weights also function, e.g., up to about 100,000.

The polyacrylic acid polymers and copolymers and partially or fully neutralized salts, e.g., metal salts, are also suitable, having monomer units:

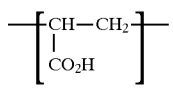

and are commercially available as CARBOPOL resins from B. F. Goodrich and PRIMAL resins from Rohm & Haas. Light cross-linking is acceptable, so long as water-solubility is retained. Weight average molecular weights, for the polyacrylic polymers and copolymers described above and below, of about 10,000 or less, e.g., 200–10,000, intercalate more easily, but higher molecular weights up to about 100,000 or more also function.

Other water-soluble derivatives of, and substituted, polyacrylic acids also are useful as intercalant polymers in accordance with the present invention, such as poly(methacrylic acid), (PMAA), having a monomeric structure:

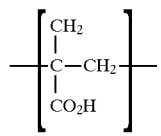

Similar water-soluble polymers and copolymers that are suitable in accordance with the present invention include poly(methacrylamide), or PMAAM, having a general monomeric structure:

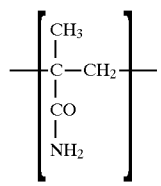

Poly(N,N-Dimethylacrylamide), having the general monomeric structure:

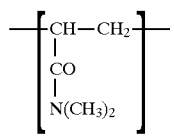

Poly(N-Isopropylacrylamide), or PIPAAm, having the monomeric structure:

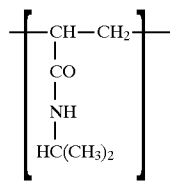

Poly(N-acetamidoacrylamide), having a monomeric structure:

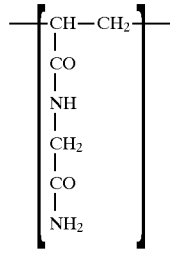

and Poly(N-acetmidomethacrylamide), having a monomeric structure:

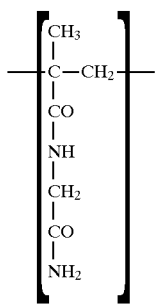

Water-soluble copolymers including any one or more of the above-described acrylic polymers also are useful in accordance with the principles of the present invention, including the acrylic interpolymers of polyacrylic acid and poly(methacrylic acid); polyacrylic acid with poly(methacrylamide); and polyacrylic acid with methacrylic acid.

Other suitable water-soluble polymers include polyvinyloxazolidone (PVO) and polyvinylmethyloxazolidone (PVMO), having the monomeric structures:

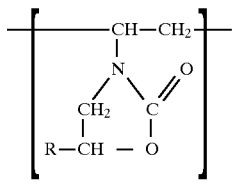

PVO: R = H
PVMO: R = CH₃

Also suitable are polyoxypropylene, polyoxyethylene block polymers that conform to the formulas:

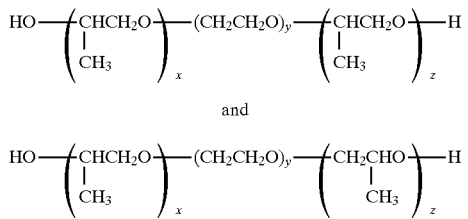

wherein x and z are each an integer in the range of about 4 to about 30; and y is an integer in the range of about 4 to about 100, for example Meroxapol 105; Meroxapol 108; Meroxapol 171; Meroxapol 172; Meroxapol 174; Meroxapol 178; Meroxapol 251; Meroxapol 252; Meroxapol 254; Meroxapol 255; Meroxapol 258; Meroxapol 311; Meroxapol 312; and Meroxapol 314.

Other suitable water-soluble/water-dispersible intercalant polymers include polyacrylamide and copolymers of acrylamide; acrylamide/sodium acrylate copolymer; acrylate/acrylamide copolymer; acrylate/ammonium methacrylate copolymer; acrylates and copolymers of acrylic acid and salts thereof; acrylate/diacetoneacrylamide copolymers; acrylic/acrylate copolymers; adipic acid/dimethylaminohydroxypropyl diethylenetriamine copolymer; aminoethylacrylate phosphate/acrylate copolymer; ammonium acrylate copolymers; ammonium styrene/acrylate copolymers; ammonium vinyl acetate/acrylate copolymers; AMP acrylate/diacetoneacrylamide copolymers; AMPD acrylate/diacetoneacrylamide copolymers; butyl benzoic acid/phthalic anhydride/trimethylolethane copolymer; butyl ester of ethylene/maleic anhydride copolymer; butyl ester of PVM/MA copolymer; calcium/sodium PVM/MA copolymer; cornstarch/acrylamide/sodium acrylate copolymer; diethylene glycolamine/epichlorohydrin/piperazine copolymer; dodecanedioic acid/cetearyl alcohol/glycol copolymers; ethylene/maleic anhydride copolymer; ethylene/vinyl alcohol copolymer; ethyl ester of PVM/MA copolymer; polyethyleneimines, such as hydroxyethyl/PEI-1000 and hydroxyethyl PEI-1500; isobutylene/maleic anhydride copolymer; isopropyl ester of PVM/MA copolymer; melamine/formaldehyde resin; methacryloyl ethyl betaine/methacrylate copolymers; methoxy PEG-22/dodecyl glycol copolymer; octadecene/maleic anhydride copolymer; octylacrylamide/acrylate/butylaminoethyl methacrylate copolymers; octylacrylamide/acrylate copolymers; PEG/dodecyl glycol copolymers; polyethyleneimines, such as PEI-7; PEI-15; PEI-30; PEI-45; PEI-275; PEI-700; PEI-1000; PEI-1500; and PEI-2500; phthalic anhydride/glycerin/glycidyl decanoate copolymer; polyacrylamidomethylpropane sulfonic acid; polyacrylic acid; polyaminopropyl biguanide; polymeric quaternary ammonium salts, such as polyquaternium-1; polyquaternium-2; polyquaternium-4; polyquaternium-5; polyquaternium-6; polyquaternium-7; polyquaternium-8; polyquaternium-9; polyquaternium-10; polyquaternium-11; polyquaternium-12; polyquaternium-13; polyquaternium-14; and polyquaternium-15; polyvinyl alcohol; polyvinyl imidazolinium acetate; potassium aluminum polyacrylate; PVM/MA copolymers; PVP/eicosene copolymers; PVP/ethyl methacrylate/methacrylic acid copolymer; PVP/hexadecene copolymer; PVP/VA copolymer; PVP/vinyl acetate/itaconic acid copolymer; sodium acrylate/vinyl alcohol copolymers; sodium $C_4$–$C_{12}$ olefin/maleic acid copolymer; sodium polymethacrylate; sodium polynaphthalene sulfonate; sodium polystyrene sulfonate; sodium styrene/acrylate/PEG-10 dimaleate copolymer; water-soluble esters and ethers of cellulose; sodium styrene/PEG-10 maleate/nonoxynol-10 maleate/acrylate copolymer; starch/acrylate/acrylamide copolymers; styrene/acrylamide copolymer; styrene/acrylate/ammonium methacrylate copolymer; styrene/maleic anhydride copolymer; styrene/PVO copolymer; sucrose benzoate/sucrose acetate isobutyrate/butyl benzyl phthalate copolymer; sucrose benzoate/sucrose acetate isobutyrate/butyl benzylphthalate/methyl methacrylate copolymer; urea/formaldehyde prepolymers; urea/melamine/formaldehyde prepolymers; vinyl acetate/crotonic acid copolymers; and vinyl alcohol copolymers.

Other water-soluble polymeric polyols and polyhydric alcohols, such as polysaccharides, also are suitable as polymer intercalants.

Suitable water-insoluble intercalant polymers include polyamides; polyesters; polycarbonates; polyurethanes; polyepoxides; polyolefins; polyalkylamides; and mixtures thereof. Suitable water-insoluble polymers include:

polyethers (polymers and copolymers) based on ethylene oxide, butylene oxide, propylene oxide, phenols and bisphenols;

polyesters (polymers and copolymers) based on aliphatic and aromatic diols, and aliphatic and aromatic dibasic acids;

polyurethanes based on aliphatic and aromatic diisocyanates, and aliphatic and aromatic diols;

polyamides (polymers and copolymers) based on (a) aliphatic and aromatic diamines, and aliphatic and aromatic dibasic acids; (b) aliphatic and aromatic amino acids;

polycarbonates (polymers and copolymers) based on carbonic acid and aromatic diols;

polycarbonimides (polymers and copolymers) based on dianhydride of tetrabasic acids and diamines and other heterochain polymers;

vinyl polymers and copolymers based on vinyl monomers, styrene and derivatives of styrene;

acryl polymers and copolymers based on acryl monomers;

copolymers based on styrene, vinyl and acryl monomers;

polyolefins polymers and copolymers based on ethylene, propylene and other alphaolefin monomers;

polymers and copolymers based on dienes, isobutylenes and the like; and copolymers based on dienes, styrene, acryl and vinyl monomers.

Thermoset resins based on water-soluble prepolymers, include prepolymers based on formaldehyde: phenols (phenol, cresol and the like); urea; melamine; melamine and phenol; urea and phenol. Polyurethanes based on: toluene diisocyanate (TDI) and monomeric and polymeric diphenyl methanediisocyanates (MDI); hydroxy terminated polyethers (polyethylene glycol, polypropylene glycol, copolymers of ethylene oxide and propylene oxide and the like); amino terminated polyethers, polyamines (tetramethylene diamine, ethylenediamine, hexamethylenediamine, 2,2-dimethyl 1,3-propanediamine; melamine, diaminobenzene, triaminobenzene and the like); polyamidoamines (for instance, hydroxy terminated polyesters); unsaturated polyesters based on maleic and fumaric anhydrides and acids; glycols (ethylene, propylene), polyethylene glycols, polypropylene glycols, aromatic glycols and polyglycols; unsaturated polyesters based on vinyl, allyl and acryl monomers; epoxides, based on biphenol A (2,2'-bis(4-hydroxyphenyl) propane) and epichlorohydrin; epoxy prepolymers based on monoepoxy and polyepoxy compounds and α,β unsaturated compounds (styrene, vinyl, allyl, acrylic monomers); polyamides 4-tetramethylene diamine, hexamethylene diamine, melamine, 1,3-propanediamine, diaminobenzene, triaminobenzene, 3,3',4,4'-bitriaminobenzene; 3,3',4,4'-biphenyltetramine and the like). Polyethyleneimines; amides and polyamides (amides of di-, tri-, and tetra acids); hydroxyphenols (pyrogallol, gallic acid, tetrahydroxybenzophenone, tetrahydroquinone, catechol, phenol and the like); anhydrides and polyanhydrides of di-, tri-, and tetra acids; polyisocyanurates based on TDI and MDI; polyimides based on pyromellitic dianhydride and 1,4-phenyldiamine; polybenzimidozoles based on 3,3',4,4'-biphenyltetramine and isophthalic acid; polyamide based on unsaturated dibasic acids and anhydrides (maleic, fumaric) and aromatic polyamides; alkyd resins based on dibasic aromatic acids or anhydrides, glycerol, trimethylolpropane, pentaerythritol, sorbitol and unsaturated fatty long chain carboxylic acids (the latter derived from vegetable oils); and prepolymers based on acrylic monomers (hydroxy or carboxy functional).

The amount of intercalated and/or exfoliated layered material included in a liquid carrier or into a matrix polymer to form viscous carriers or a composite polymeric material may vary widely depending on the intended use of the material. When the intercalate or exfoliate is added to a solvent to form the viscous compositions suitable to deliver the carrier or some carrier-dissolved or carrier-dispersed active material, such as a pharmaceutical, relatively higher amounts of intercalates, i.e., from about 10%.t to about 30% by weight of the total composition, are used in forming solvent gels having extremely high viscosities, e.g., 5,000 to 5,000,000 centipoises. Extremely high viscosities, however, also can be achieved with a relatively small concentration of intercalates and/or exfoliates thereof, e.g., 0.1% to 5% by weight, by adjusting the pH of the composition in the range of about 0–6 or about 10–14 and/or by heating the composition above room temperature, e.g., in the range of about 25° C. to about 200° C., preferably about 75° C. to about 100° C.

Relatively larger amounts of platelet particles (exclusive of the intercalant polymer, since the intercalant polymer content in the layered material may vary), i.e., from about 15% to about 30% by weight of the mixture, are used in applications when the intercalate and/or exfoliate is added to a matrix polymer and the composite material is used to form stamped polymeric articles. Substantially enhanced barrier properties and heat resistance (deflection temperature under load, DTUL) are imparted by platelet particle concentrations greater than about 2.5% in a matrix polymer. Similarly, substantially enhanced strength is imparted by platelet particle concentrations greater than about 1.5%, including the nano-scale layered materials of this invention. It is preferred that the platelet loading be less than about 10%. Platelet particle loadings within the range of about 0.05% to about 40% by weight, preferably about 0.5% to about 20%, more preferably about 1% to about 10% of the composite material significantly enhances modulus, dimensional stability, and wet strength. In general, the amount of platelet particles incorporated into a matrix polymer is less than about 90% by weight of the mixture, and preferably from about 0.01% to about 80% by weight of the composite material mixture, more preferably from about 0.05% to about 40% by weight of the polymer/particle mixture, and most preferably from about 0.05% to about 20% or 0.05% to about 10% by weight, with some matrix polymers.

In accordance with an important feature of the present invention, the intercalated phyllosilicate can be manufactured in a concentrated form, e.g., 10–90%, preferably 20–80% intercalant polymer and 10–90%, preferably 20–80% intercalated phyllosilicate that can be dispersed in a solvent or matrix polymer and exfoliated before or after addition to the solvent or to a polymer melt to a desired platelet loading. The intercalates are exfoliated and dispersed into a host material, such as an organic solvent or one or more melt-processible thermoplastic and/or thermosetting matrix oligomers or polymers, or mixtures thereof.

In accordance with an important feature of the present invention, a wide variety of topically-active compounds can be incorporated into a stable composition of the present invention. Such topically active compositions include cosmetic, industrial, and medicinal compounds that act upon contact with the skin or hair, or are used to adjust rheology of industrial greases and the like. In accordance with another important feature of the present invention, a topically-active compound can be solubilized in the composition of the present invention or can be homogeneously dispersed throughout the composition as an insoluble, particulate material. In either case topically-effective compositions of the present invention are resistant to composition separation and effectively apply the topically-active compound to the skin or hair. If required for stability, a surfactant can be included in the composition, such as any disclosed in Laughlin, et al. U.S. Pat. No. 3,929,678, hereby incorporated by reference. In general, the topically-effective compositions of the present invention demonstrate essentially no phase separation if the topically-active compound is solubilized in the compositions. Furthermore, if the topically-active compound is insoluble in the composition, the composition demonstrates essentially no phase separation.

The topically-active compounds can be a cosmetically-active compound, a medically-active compound or any other compound that is useful upon application to the skin or hair. Such topically-active compounds include, for example, antiperspirants, antidandruff agents, antibacterial compounds, antifungal compounds, anti-inflammatory compounds, topical anesthetics, sunscreens and other cosmetic and medical topically-effective compounds.

Therefore, in accordance with an important feature of the present invention, the stable topically-effective composition can include any of the generally-known antiperspirant compounds such as finely-divided solid astringent salts, for example, aluminum chlorohydrate, aluminum chlorohydrox, zirconium chlorohydrate, and complexes of aluminum chlorohydrate with zirconyl chloride or zirconyl hydroxychloride. In general, the amount of the antiperspirant compound, such as aluminum zirconium tetrachlorohydrex glycine in the composition can range from about 0.01% to about 50%, and preferably from about 0.1% to about 30%, by weight of the total composition.

Other topically-active compounds can be included in the compositions of the present invention in an amount sufficient to perform their intended function. For example, zinc oxide, titanium dioxide or similar compounds can be included if the composition is intended to be a sunscreen. Similarly, topically-active drugs, like antifungal compounds; antibacterial compounds; anti-inflammatory compounds; topical anesthetics; skin rash, skin disease and dermatitis medications; and anti-itch and irritation-reducing compounds can be included in the compositions of the present invention. For example, analgesics such as benzocaine, dyclonine hydrochloride, aloe vera and the like; anesthetics such as butamben picrate, lidocaine hydrochloride, zylocaine and the like; antibacterials and antiseptics, such as povidone-iodine, polymyxin b sulfate-bacitracin, zinc-neomycin sulfate-hydrocortisone, chloramphenicol, methylbenzethonium chloride, and erythromycin and the like; antiparasitics, such as lindane; deodorants, such as chlorophyllin copper complex, aluminum chloride, aluminum chloride hexahydrate, and methylbenzethonium chloride; essentially all dermatologicals, like acne preparations, such as benzoyl peroxide, erythromycin-benzoyl peroxide, clindamycin phosphate, 5,7-dichloro-8-hydroxyguinoline, and the like; anti-inflammatory agents, such as alclometasone dipropionate, betamethasone valerate, and the like; burn relief ointments, such as o-amino-p-toluenesulfonamide monoacetate and the like; depigmenting agents, such as monobenzone; dermatitis relief agents, such as the active steroids amcinonide, diflorasone diacetate, hydrocortisone, and the like; diaper rash relief agents, such as methylbenzethonium chloride and the like; emollients and moisturizers, such as mineral oil, PEG-4 dilaurate, lanolin oil, petrolatum, mineral wax and the like; fungicides, such as butocouazole nitrate, haloprogin, clotrimazole, and the like; herpes treatment drugs, such as 9-[(2-hydroxyethoxy)methyl]guanine; pruritic medications, such as alclometasone dipropionate, betamethasone valerate, isopropyl myristate MSD, and the like; psoriasis, seborrhea and scabicide agents, such as anthralin, methoxsalen, coal tar and the like; sunscreens, such as octyl p-(dimethylamino)benzoate, octyl methoxycinnamate, oxybenzone and the like; steroids, such as 2-(acetyloxy)-9-fluoro-1',2',3',4'-tetrahydro-11-hydroxypregna-1,4-dieno [16,17-b]naphthalene-3,20-dione, and 21-chloro-9-fluoro-1',2',3',4'-tetrahydro-11b-hydroxypregna-1,4-dieno[16z,17-b]naphthalene-3,20-dione. Any other medication capable of topical administration also can be incorporated in composition of the present invention in an amount sufficient to perform its intended function.

Matrix polymers for use in the process of this invention may vary widely, the only requirement is that they are melt processible. In the preferred embodiments of the invention, the polymer includes at least 10, preferably at least 30 recurring monomeric units. The upper limit to the number of recurring monomeric units is not critical, provided that the melt index of the matrix polymer under use conditions is such that the matrix polymer forms a flowable mixture. Most preferably, the matrix polymer includes from at least about 10 to about 100 recurring monomeric units. In the most preferred embodiments of this invention, the number of recurring units is such that the matrix polymer has a melt index of from about 0.01 to about 12 grams per 10 minutes at the processing temperature.

Thermoplastic resins and rubbers for use as matrix polymers in the practice of this invention may vary widely. Illustrative of useful thermoplastic resins, which may be used alone or in admixture, are polylactones such as poly (pivalolactone), poly(caprolactone) and the like; polyurethanes derived from reaction of diisocyanates such as 1,5-naphthalene diisocyanate; p-phenylene diisocyanate, m-phenylene diisocyanate, 2,4-toluene diisocyanate, 4,4'-diphenylmethane diisocyanate, 3,3'-dimethyl-4,4'-biphenyl diisocyanate, 4,4'-diphenylisopropylidene diisocyanate, 3,3'-dimethyl-4,4'-diphenyl diisocyanate, 3,3'-dimethyl-4,4'-diphenylmethane diisocyanate, 3,3'-dimethoxy-4,4'-biphenyl diisocyanate, dianisidine diisocyanate, toluidine diisocyanate, hexamethylene diisocyanate, 4,4'-diisocyanatodiphenylmethane and the like and linear long-chain hydroxy terminated polyesters; polyethers based on diols, such as poly(tetramethylene adipate), poly(ethylene adipate), poly(1,4-butylene adipate), poly(ethylene succinate), poly(2,3-butylene succinate), polyether diols and the like; polycarbonates such as poly[methane bis(4-phenyl) carbonate], poly[1,1-ether bis(4-phenyl) carbonate], poly [diphenylmethane bis(4-phenyl)carbonate], poly[1,1-cyclohexane bis(4-phenyl)carbonate] and the like; polysulfones; polyethers; polyketones; polyamides such as poly(4-amino butyric acid), poly(hexamethylene adipamide), poly (6-aminohexanoic acid), poly(m-xylylene adipamide), poly (p-xylylene sebacamide), poly(2,2,2-trimethyl hexamethylene terephthalamide), poly(metaphenylene isophthalamide) (NOMEX), poly(p-phenylene terephthalamide) (KEVLAR), and the like; polyesters such as poly(ethylene azelate), poly(ethylene-1,5-naphthalate, poly(1,4-cyclohexane dimethylene terephthalate), poly (ethylene oxybenzoate) (A-TELL), poly(para-hydroxy benzoate) (EKONOL), poly(1,4-cyclohexylidene dimethylene terephthalate) (KODEL) (Cis), poly(1,4-cyclohexylidene dimethylene terephthalate) (Kodel) (trans), polyethylene terephthlate, polybutylene terephthalate and the like; poly(arylene oxides) such as poly(2,6-dimethyl-1, 4-phenylene oxide), poly(2,6-diphenyl-1,4-phenylene oxide) and the like; poly(arylene sulfides) such as poly (phenylene sulfide) and the like; polyetherimides; vinyl polymers and their copolymers such as polyvinyl acetate, polyvinyl alcohol, polyvinyl chloride; polyvinyl butyral, polyvinylidene chloride, ethylene-vinyl acetate copolymers, and the like; polyacrylics, polyacrylate and their copolymers such as polyethyl acrylate, poly(n-butyl acrylate), polymethylmethacrylate, polyethyl methacrylate, poly(n-butyl methacrylate), poly(n-propyl methacrylate), polyacrylamide, polyacrylonitrile, polyacrylic acid, ethylene-acrylic acid copolymers, ethylene-vinyl alcohol copolymers acrylonitrile copolymers, methyl methacrylate-styrene copolymers, ethylene-ethyl acrylate copolymers, methacrylated butadiene-styrene copolymers and the like;

polyolefins such as low density poly(ethylene), poly (propylene), chlorinated low density poly(ethylene), poly(4-methyl-1-pentene), poly(ethylene), poly(styrene), and the like; ionomers; poly(epichlorohydrins); poly(urethane) such as the polymerization product of diols, such as ethylene glycol, propylene glycol, and/or a polydiol, such as diethylene glycol, triethylene glycol and/or tetraethylene glycol, and the like, with a polyisocyanate such as 2,4-tolylene diisocyanate, 2,6-tolylene diisocyante, 4,4'-diphenylmethane diisocyanate, 1,6-hexamethylene diisocyanate, 4,4'-dicyclohexylmethane diisocyanate and the like; and polysulfones such as the reaction product of the sodium salt of 2,2-bis(4-hydroxyphenyl) propane and 4,4'-dichlorodiphenyl sulfone; furan resins such as poly(furan); cellulose ester plastics such as cellulose acetate, cellulose acetate butyrate, cellulose propionate and the like; silicones such as poly(dimethyl siloxane), poly(dimethyl siloxane co-phenylmethyl siloxane), and the like; protein plastics; and blends of two or more of the foregoing.

Vulcanizable and thermoplastic rubbers useful in the practice of this invention may also vary widely. Illustrative of such rubbers are brominated butyl rubber, chlorinate butyl rubber, polyurethane elastomers, fluoroelastomers, polyester elastomers, polyvinylchloride, butadiene/acrylonitrile elastomers, silicone elastomers, poly(butadiene), poly (isobutylene), ethylene-propylene copolymers, ethylene-propylene-diene terpolymers, sulfonated ethylene-propylene-diene terpolymers, poly(chloroprene), poly(2,3-dimethylbutadiene), poly(butadiene-pentadiene), chlorosulphonated poly(ethylenes), poly(sulfide) elastomers, block copolymers, made up of segments of glassy or crystalline blocks such as poly(styrene), poly (vinyl-toluene), poly(t-butyl styrene), polyesters and the like and the elastomeric blocks such as poly(butadiene), poly (isoprene), ethylene-propylene copolymers, ethylene-butylene copolymers, polyether and the like as for example the copolymers in poly(styrene)-poly(butadiene)-poly (styrene) block copolymer manufactured by Shell Chemical Company under the trade name KRATON®.

Useful thermosetting resins include, for example, the polyamides; polyalkylamides; polyesters; polyurethanes; polycarbonates; polyepoxides; and mixtures thereof. Thermoset resins based on water-soluble prepolymers, include prepolymers based on formaldehyde: phenols (phenol, cresol and the like); urea; melamine; melamine and phenol; urea and phenol. Polyurethanes based on: toluene diisocyanate (TDI) and monomeric and polymeric diphenyl methanediisocyanates (MDI); hydroxy terminated polyethers (polyethylene glycol, polypropylene glycol, copolymers of ethylene oxide and propylene oxide and the like); amino terminated polyethers, polyamines (tetramethylene diamine, ethylenediamine, hexamethylenediamine, 2,2-dimethyl 1,3-propanediamine; melamine, diaminobenzene, triaminobenzene and the like); polyamidoamines (for instance, hydroxy terminated polyesters); unsaturated polyesters based on maleic and fumaric anhydrides and acids; glycols (ethylene, propylene), polyethylene glycols, polypropylene glycols, aromatic glycols and polyglycols; unsaturated polyesters based on vinyl, allyl and acryl monomers; epoxides, based on biphenol A (2,2'-bis(4-hydroxyphenyl) propane) and epichlorohydrin; epoxy prepolymers based on monoepoxy and polyepoxy compounds and α,β unsaturated compounds (styrene, vinyl, allyl, acrylic monomers); polyamides 4-tetramethylene diamine, hexamethylene diamine, melamine, 1,3-propanediamine, diaminobenzene, triaminobenzene, 3,3',4,4'-bitriaminobenzene; 3,3',4,4'-biphenyltetramine and the like). Polyethyleneimines; amides and polyamides (amides of di-, tri-, and tetra acids); hydroxyphenols (pyrogallol, gallic acid, tetrahydroxybenzophenone, tetrahydroquinone, catechol, phenol and the like); anhydrides and polyandrides of di-, tri-, and tetraacids; polyisocyanurates based on TDI and MDI; polyimides based on pyromellitic dianhydride and 1,4-phenyldiamine; polybenzimidozoles based on 3,3',4,4'-biphenyltetramine and isophthalic acid; polyamide based on unsaturated dibasic acids and anhydrides (maleic, fumaric) and aromatic polyamides; alkyd resins based on dibasic aromatic acids or anhydrides, glycerol, trimethylolpropane, pentaerythritol, sorbitol and unsaturated fatty long chain carboxylic acids (the latter derived from vegetable oils); and prepolymers based on acrylic monomers (hydroxy or carboxy functional).

Most preferred thermoplastic polymers are thermoplastic polymers such as polyamides, polyesters, and polymers of alpha-beta unsaturated monomers and copolymers. Polyamides which may be used in the process of the present invention are synthetic linear polycarbonamides characterized by the presence of recurring carbonamide groups as an integral part of the polymer chain which are separated from one another by at least two carbon atoms. Polyamides of this type include polymers, generally known in the art as nylons, obtained from diamines and dibasic acids having the recurring unit represented by the general formula:

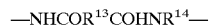

—NHCOR$^{13}$COHNR$^{14}$— in which $R^{13}$ is an alkylene group of at least 2 carbon atoms, preferably from about 2 %o about 11, or arylene having at least about 6 carbon atoms, preferably about 6 to about 17 carbon atoms; and $R^{14}$ is selected from $R^{13}$ and aryl groups. Also, included are copolyamides and terpolyamides obtained by known methods, for example, by condensation of hexamethylene diamine and a mixture of dibasic acids consisting of terephthalic acid and adipic acid. Polyamides of the above description are well-known in the art and include, for example, the copolyamide of 30% hexamethylene diammonium isophthalate and 70% hexamethylene diammonium adipate, poly(hexamethylene adipamide) (nylon 6,6), poly(hexamethylene sebacamide) (nylon 6, 10), poly(hexamethylene isophthalamide), poly(hexamethylene terephthalamide), poly(heptamethylene pimelamide) (nylon 7,7), poly(octamethylene sebacamide) (nylon 8,8), poly (nonamethylene azelamide) (nylon 9,9) poly(decamethylene azelamide) (nylon 10,9), poly(decamethylene sebacamide) (nylon 10,10), poly[bis(4-amino cyclohexyl)methane-1,10-decanecarboxamide)], poly(m-xylylene adipamide), poly(p-xylylene sebacamide), poly(2,2,2-trimethyl hexamethylene terephthalamide), poly(piperazine sebacamide), poly(p-phenylene terephthalamide), poly(metaphenylene isophthalamide) and the like.

Other useful polyamides are those formed by polymerization of amino acids and derivatives thereof, as, for example, lactams. Illustrative of these useful polyamides are poly(4-aminobutyric acid) (nylon 4), poly(6-aminohexanoic acid) (nylon 6), poly(7-aminoheptanoic acid) (nylon 7), poly(8-aminooctanoic acid) (nylon 8), poly(9-aminononanoic acid) (nylon 9), poly (10-aminodecanoic acid) (nylon 10), poly(11-aminoundecanoic acid) (nylon 11), poly(12-aminododecanoic acid) (nylon 12) and the like.

Preferred polyamides are poly(caprolactam), poly(12-aminododecanoic acid) and poly(hexamethylene adipamide).

Other matrix or host polymers which may be employed in admixture with exfoliates to form nanocomposites are linear polyesters. The type of polyester is not critical and the particular polyesters chosen for use in any particular situation will depend essentially on the physical properties and features, i.e., tensile strength, modulus and the like, desired in the final form. Thus, a multiplicity of linear thermoplastic polyesters having wide variations in physical properties are suitable for use in admixture with exfoliated layered material platelets in manufacturing nanocomposites in accordance with this invention.

The particular polyester chosen for use can be a homopolyester or a co-polyester, or mixtures thereof, as desired. Polyesters are normally prepared by the condensation of an organic dicarboxylic acid and an organic diol, and, the reactants can be added to the intercalates, or exfoliated intercalates for in situ polymerization of the polyester while in contact with the layered material, before or after exfoliation of the intercalates.

Polyesters which are suitable for use in this invention are those which are derived from the condensation of aromatic, cycloaliphatic, and aliphatic diols with aliphatic, aromatic and cycloaliphatic dicarboxylic acids and may be cycloaliphatic, aliphatic or aromatic polyesters.

Exemplary of useful cycloaliphatic, aliphatic and aromatic polyesters which can be utilized in the practice of their invention are poly(ethylene terephthalate), poly(cyclohexylenedimethylene terephthalate), poly(ethylene dodecate), poly(butylene terephthalate), poly[ethylene(2,7-naphthalate)], poly(methaphenylene isophthalate), poly(glycolic acid), poly(ethylene succinate), poly(ethylene adipate), poly(decamethylene azelate), poly(ethylene sebacate), poly(decamethylene adipate), poly(decamethylene sebacate), poly(dimethylpropiolactone), poly(para-hydroxybenzoate) (EKONOL), poly(ethylene oxybenzoate) (A-tell), poly(ethylene isophthalate), poly(tetramethylene terephthalate, poly(hexamethylene terephthalate), poly(decamethylene terephthalate), poly(1,4-cyclohexane dimethylene terephthalate) (trans), poly(ethylene 1,5-naphthalate), poly(ethylene 2,6-naphthalate), poly(1,4-cyclohexylidene dimethylene terephthalate), (KODEL) (cis), and poly(1,4-cyclohexylidene dimethylene terephthalate (KODEL) (trans).

Polyester compounds prepared from the condensation of a diol and an aromatic dicarboxylic acid are especially suitable in accordance with the present invention. Illustrative of such useful aromatic carboxylic acids are terephthalic acid, isophthalic acid and a o-phthalic acid, 1,3-naphthalenedicarboxylic acid, 1,4-naphthalenedicarboxylic acid, 2,6-naphthalenedicarboxylic acid, 2,7-naphthalene-dicarboxylic acid, 4,4'-diphenyldicarboxylic acid, 4,4'-diphenylsulfone-dicarboxylic acid, 1,1,3-trimethyl-5-carboxy-3-(p-carboxyphenyl)-idane, diphenyl ether 4,4'-dicarboxylic acid, bis-p(carboxyphenyl) methane and the like. Of the aforementioned aromatic dicarboxylic acids, those based on a benzene ring (such as terephthalic acid, isophthalic acid, orthophthalic acid) are preferred for use in the practice of this invention. Amongst these preferred acid precursors, terephthalic acid is particularly preferred acid precursor.

The most preferred embodiments of this invention incorporate the intercalate into a polymer selected from the group consisting of poly(ethylene terephthalate), poly(butylene terephthalate), poly(1,4-cyclohexane dimethylene terephthalate), a polyvinylimine, and mixture thereof. Among these polyesters of choice, poly(ethylene terephthalate) and poly(butylene terephthalate) are most preferred.

Still other useful thermoplastic homopolymers and copolymer matrix polymers for forming nanocomposites are polymers formed by polymerization of alpha-beta-unsaturated monomers or the formula:

$$R^{15}R^{16}C=CH_2$$

wherein:

$R^{15}$ and $R^{16}$ are the same or different and are cyano, phenyl, carboxy, alkylester, halo, alkyl, alkyl substituted with one or more chloro or fluoro, or hydrogen. Illustrative of such preferred homopolymers and copolymers are homopolymers and copolymers of ethylene, propylene, vinyl alcohol, acrylonitrile, vinylidene chloride, esters of acrylic acid, esters of methacrylic acid, chlorotrifluoroethylene, vinyl chloride and the like. Preferred are poly(propylene), propylene copolymers, poly(ethylene) and ethylene copolymers. More preferred are poly(ethylene) and poly(propylene).

In the preferred embodiments of the invention, the matrix polymers of choice in manufacturing nanocomposites are polymers and copolymers of olefins, polyesters, polyamides, polyvinylimines, and blends thereof containing polyesters. In the particularly preferred embodiments of the invention, polymers and copolymers of ethylene, polyamides (preferably nylon 6 and nylon 66 and more preferably nylon 6), and blends thereof are used.

The mixture may include various optional components which are additives commonly employed with polymers. Such optional components include nucleating agents, fillers, plasticizers, impact modifiers, chain extenders, plasticizers, colorants, mold release lubricants, antistatic agents, pigments, fire retardants, and the like. These optional components and appropriate amounts are well known to those skilled in the art.

Exfoliation of the intercalated layered material should provide delamination of at least about 90% by weight of the intercalated material to provide a composition comprising a polymeric matrix having platelet particles substantially homogeneously dispersed therein. Some intercalates require a shear rate that is greater than about 10 sec$^{-1}$ for such relatively thorough exfoliation. Other intercalates exfoliate naturally or by heating to the melt temperature of the intercalant polymer, or by applying pressure, e.g., 0.5 to 60 atmospheres above ambient, with or without heating. The upper limit for the shear rate is not critical provided that the shear rate is not so high as to physically degrade the polymer. In the particularly preferred embodiments of the invention, when shear is employed for exfoliation, the shear rate is from greater than about 10 sec$^{-1}$ to about 20,000 sec$^{-1}$, and in the more preferred embodiments of the invention the shear rate is from about 100 sec$^{-1}$ to about 10,000 sec$^{-1}$.

When shear is employed for exfoliation, any method which can be used to apply a shear to a flowable mixture or any polymer melt can be used. The shearing action can be provided by any appropriate method, as for example by mechanical means, by thermal shock, by pressure alteration, or by ultrasonics, all known in the art. In particularly useful procedures, the flowable polymer mixture is sheared by mechanical methods in which portions of the melt are caused to flow past other portions of the mixture by use of mechanical means, such as stirrers, Banbury® type mixers, Brabender® type mixers, long continuous mixers, and extruders. Another procedure employs thermal shock in which shearing is achieved by alternatively raising or lowering the temperature of the mixture causing thermal expansions and resulting in internal stresses which cause the shear. In still other procedures, shear is achieved by sudden pressure changes in pressure alteration methods; by ultrasonic techniques in which cavitation or resonant vibrations which cause portions of the mixture to vibrate or to be excited at different phases and thus subjected to shear. These methods of shearing flowable polymer mixtures and polymer melts are merely representative of useful methods, and any method known in the art for shearing flowable polymer mixtures and polymer melts may be used.

Mechanical shearing methods may be employed such as by extrusion, injection molding machines, Banbury® type mixers, Brabender® type mixers and the like. Shearing also can be achieved by introducing the polymer melt at one end of the extruder (single or double screw) and receiving the sheared polymer at the other end of the extruder. The temperature of the polymer melt, the length of the extruder, residence time of the melt in the extruder and the design of the extruder (single screw, twin screw, number of flights per unit length, channel depth, flight clearance, mixing zone, etc.) are several variables which control the amount of shear to be applied.

Exfoliation should be sufficiently thorough to provide at least about 80% by weight, preferably at least about 85% by weight, more preferably at least about 90% by weight, and most preferably at least about 95% by weight delamination of the layers to form platelet particles substantially homogeneously dispersed in the polymer matrix. As formed by this process, the platelet particles dispersed in matrix polymers have the thickness of the individual layers, or small multiples less than about 10, preferably less than about 5 and more preferably less than about 3 of the layers, and still more preferably 1 or 2 layers. In the preferred embodiments of this invention, intercalation and delamination of every interlayer space is complete so that all or substantially all individual layers delaminate one from the other to form separate platelet particles. In cases where intercalation is incomplete between some layers, those layers will not delaminate in a polymer melt, and will form platelet particles comprising those layers in a coplanar aggregate.

The effect of adding into a matrix polymer the nanoscale particulate dispersed platelet particles, derived from the intercalates formed in accordance with the present invention, typically is an increase in tensile modulus and ultimate tensile strength or an increase in ultimate impact resistance or glass transition temperature (Tg).

Molding compositions comprising a thermoplastic or thermosetting polymer containing a desired loading of platelets obtained from exfoliation of the intercalates manufactured according to the invention are outstandingly suitable for the production of sheets and panels having valuable properties. Such sheets and panels may be shaped by conventional processes such as vacuum processing or by hot pressing to form useful objects. The sheets and panels according to the invention are also suitable as coating materials for other materials comprising, for example, wood, glass, ceramic, metal or other plastics, and outstanding strengths can be achieved using conventional adhesion promoters, for example, those based on vinyl resins. The sheets and panels can also be laminated with other plastic films and this is preferably effected by co-extrusion, the sheets being bonded in the molten state. The surfaces of the sheets and panels, including those in the embossed form, can be improved or finished by conventional methods, for example by lacquering or by the application of protective films.

The polymer/platelet composite materials are especially useful for fabrication of extruded films and film laminates, as for example, films for use in food packaging. Such films can be fabricated using conventional film extrusion techniques. The films are preferably from about 10 to about 100 microns, more preferably from about 20 to about 100 microns and most preferably from about 25 to about 75 microns in thickness.

The homogeneously distributed platelet particles and matrix polymer that form the nanocomposites are formed into a film by suitable film-forming methods. Typically, the composition is melted and forced through a film forming die. The film of the nanocomposite may go through steps to cause the platelets to be further oriented so the major planes through the platelets are substantially parallel to the major plane through the film. A method to do this is to biaxially stretch the film. For example, the film is stretched in the axial or machine direction by tension rollers pulling the film as it is extruded from the die. The film is simultaneously stretched in the transverse direction by clamping the edges of the film and drawing them apart. Alternatively, the film is stretched in the transverse direction by using a tubular film die and blowing the film up as it passes from the tubular film die. The films may exhibit one or more of the following benefits: increased modulus; increased wet strength; increased dimensional stability; decreased moisture adsorption; decreased permeability to gases such as oxygen and liquids, such as water, alcohols and other solvents.

The following specific examples are presented to more particularly illustrate the invention and are not to be construed as limitations thereon.

EXAMPLE 1

Preparation of Clay—PVP Complexes (Intercalates)

Materials:
    Clay—sodium montmorillonite;
    PVP—molecular weights of 10,000 and 40,000.

To prepare Clay (sodium montmorillonite)—PVP complexes (intercalates) we used three different processes for polymer intercalation:

1. Mixture of the 2% PVP/water solution with the 2% clay/water suspension in a ratio sufficient to provide a polymer concentration of at least about 16% based on the dry wight of the clay.
2. Dry clay powder (about 8% by weight moisture) was gradually added to the 2% PVP/water solution in a ratio sufficient to provide a polymer concentration of at least about 16% based on the weight of the clay.
3. Dry PVP was mixed with dry clay, the mixture was hydrated with 35–38% of water, based on the dry weight of the clay, and then extruded.

Mixtures 1 and 2 were agitated at room temperature during 4 hours.

The weight ratio Clay:PVP was changed from 80:20 to 20:80.

These experiments show that all methods of preparation yielded the Clay—PVP complexes (intercalates), and the results of the intercalation do not depend on the method of preparation (1, 2, or 3) or molecular weight of the intercalant polymer (PVP), but do depend on the quantity of PVP sorbed between clay platelets. In Table 1 the results of the X-ray diffraction for Clay—PVP complexes with different ratios of components are demonstrated. The plot of these data is shown in FIG. 1. From these data (Table 1, FIG. 1) one can see the step character of intercalation while the polymer is being sorbed in the interlayer space between adjacent platelets of the montmorillonite clay. There are increasing d(001) values from 12 Å for clay with no PVP sorbed to 24–25 Å spacing between adjacent platelets with sorption of 20–30% PVP. The next step to 30–32 Å spacing occurs when the sorbed PVP content is increased to 40–60%. Further increasing the sorbed PVP content to 70–80% increases the d(001) values to 40–42 Å. There are d(002) reflexes together with d(001) reflexes in X-ray patterns of all complexes obtained (Table 1, FIG. 1). This indicates the regularity of Clay—PVP complex structures.

TABLE 1

|    | PVP, %* | d(001), Å | d(002), Å |
|----|---------|-----------|-----------|
| 1  | 0.0     | 12.4      | 6.2       |
| 2  | 20.0    | 24.0      | 11.4      |
| 3  | 30.0    | 25.0      | 12.0      |
| 4  | 40.0    | 30.0      | 15.2      |
| 5  | 45.0    | 31.0      | 15.2      |
| 6  | 50.0    | 30.0      | 15.5      |
| 7  | 55.0    | 32.0      | 16.5      |
| 8  | 60.0    | 34.0      | 17.0      |
| 9  | 70.0    | 40.0      | 21.0      |
| 10 | 80.0    | 42.0      | 21.0      |

*Percent by weight, based on the dry weight of the clay.

EXAMPLE 2

Preparation of Clay—PVA Complexes (Intercalates)

Materials:
  Clay—sodium montmorillonite;
  PVA—degree of hydrolysis 75–99%, —molecular weights of 5,000 and 8,000.

To prepare Clay (sodium montmorillonite)—PVA complexes (intercalates) we provided three different processes for polymer intercalation:

1. Mixture of the 2% PVA/water solution with the 2% clay/water suspension in a ratio sufficient to provide a polymer concentration of at least about 16% based on the dry wight of the clay.
2. Dry clay powder was gradually added to the 2% PVA/water solution in a ratio sufficient to provide a polymer concentration of at least about 16% based on the weight of the clay.
3. Dry clay was moisturized with PVA/water solution to a moisture content of 20–80% water, and then extruded.

The mixtures 1 and 2 were agitated at room temperature during 4 hours.

The weight ratio Clay:PVA was changed from 80:20 to 20:80.

Figure 2:
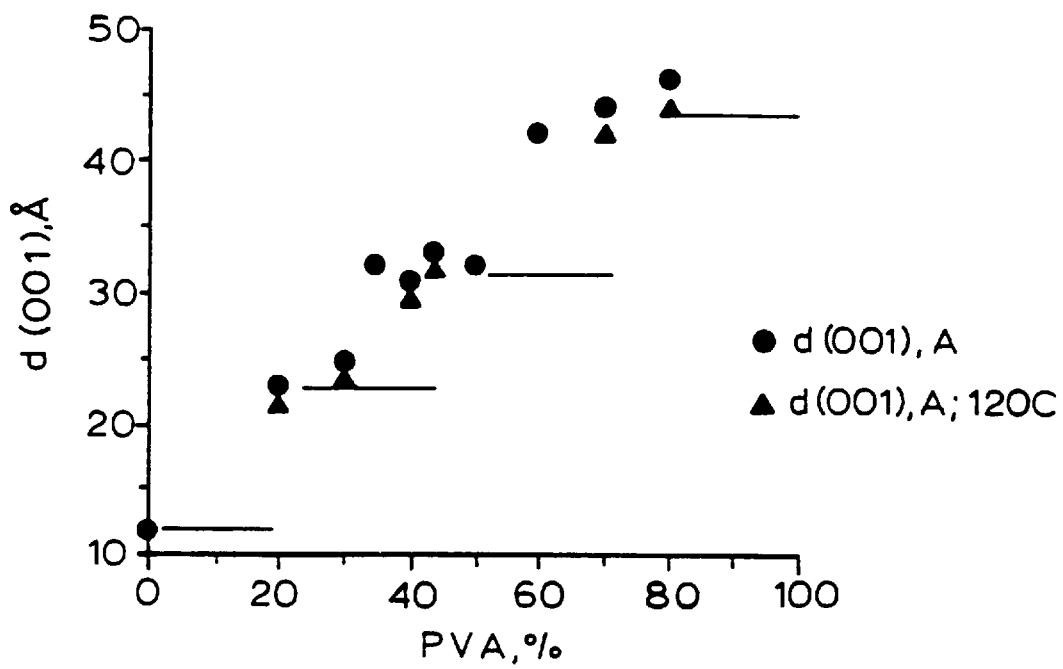
FIG. 2 is a graph plotting interlayer space for polyvinylalcohol (PVA):smectite clay complexes (intercalates) showing d(001) spacing, in Angstroms, between smectite clay platelets versus percentage of PVA sorbed, based on the dry weight of the smectite clay.

Some of the exfoliates were studied by X-ray diffraction. These experiments show that all methods of preparation yielded the composite Clay—PVA complexes (intercalates), and the results of the intercalation do not depend on the method of preparation (1, 2, or 3), or molecular weight of the intercalant polymer (PVA), or degree of hydrolysis, but do depend on the concentration of PVA sorbed between clay platelets. In Table 2 %he results of the X-ray diffraction for Clay—PVA complexes with different ratios of components are demonstrated. The plot of these data is shown in FIG. 2. From these data (Table 2, FIG. 2) one can see the step character of increasing d(001) values from 12 Å for clay with no sorbed PVA to 22–25 Å spacing between adjacent platelets with sorption of 20–30% PVA. The next step to 30–33 Å occurs when the sorbed PVA content increases to 35–50%. A further increase of the sorbed PVA content to 60–80% increases the d(001) values to 40–45 Å.

Heating of samples at 120° C. during 4 hours insignificantly changed the d(001) values (Table 2, FIG. 2).

TABLE 2

|    | PVA %* | d(001), Å | d(001), Å 120° C. |
|----|--------|-----------|-------------------|
| 1  | 0.0    | 12.4      |                   |
| 2  | 20.0   | 23.0      | 22.0              |
| 3  | 30.0   | 25.0      | 24.0              |
| 4  | 35.0   | 32.0      | 32.0              |
| 5  | 40.0   | 31.0      | 30.0              |
| 6  | 45.0   | 33.0      | 32.0              |
| 7  | 50.0   | 32.0      | 32.0              |
| 8  | 60.0   | 42.0      | 42.0              |
| 9  | 70.0   | 44.0      | 42.0              |
| 10 | 80.0   | 45.0      | 44.0              |

*Percent by weight, based on the dry weight of the clay.

Figure 3:
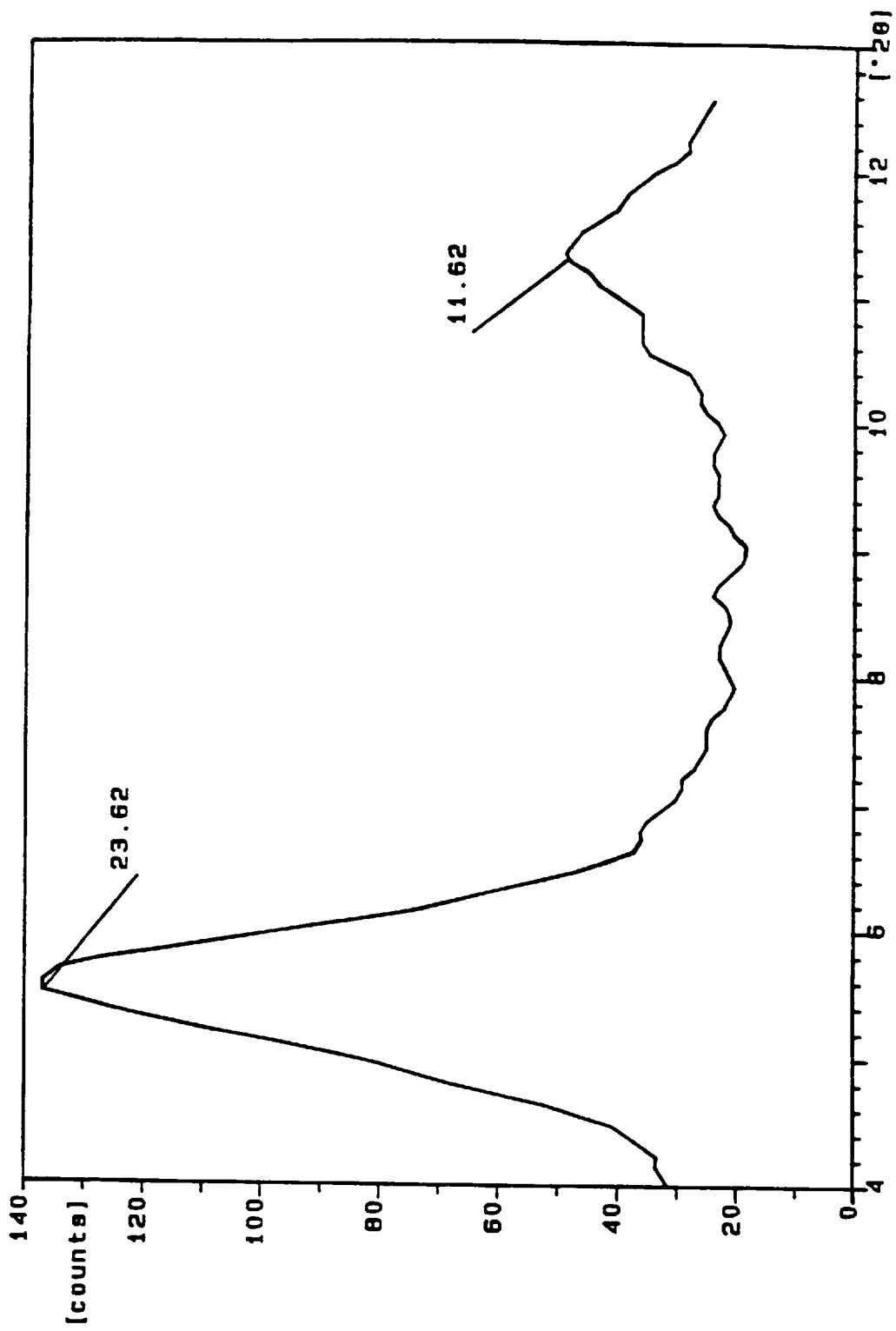
FIG. 3 is an x-ray diffraction pattern for a complex of PVP (weight average molecular weight of 10,000):sodium montmorillonite clay, in Angstroms, at a weight ratio of PVP:clay of 20:80.
Figure 4:
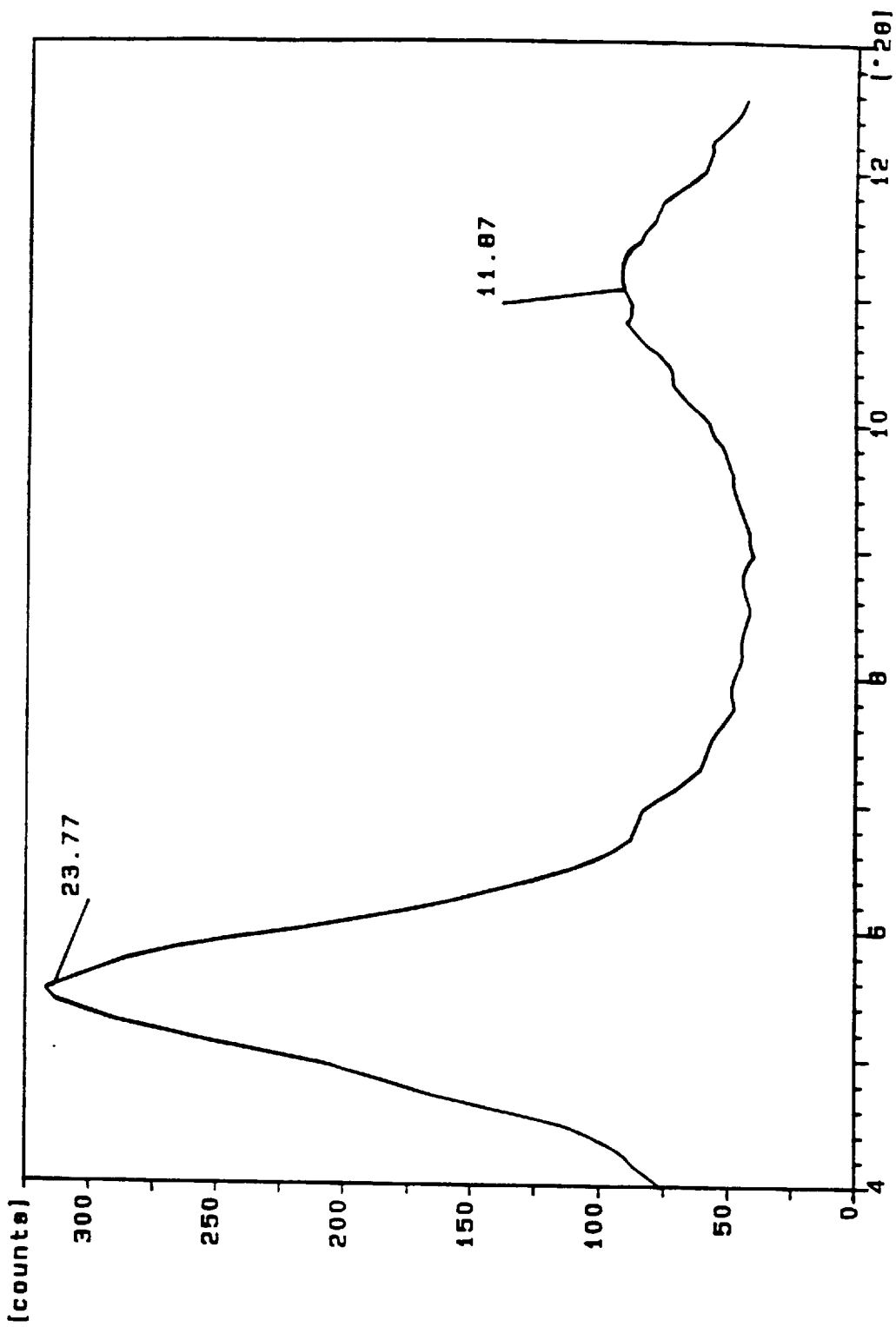
FIG. 4 is an x-ray diffraction pattern for a complex of PVP (weight average molecular weight of 40,000):sodium montmorillonite clay, in Angstroms, at a weight ratio of PVP:clay of 20:80.
Figure 5:
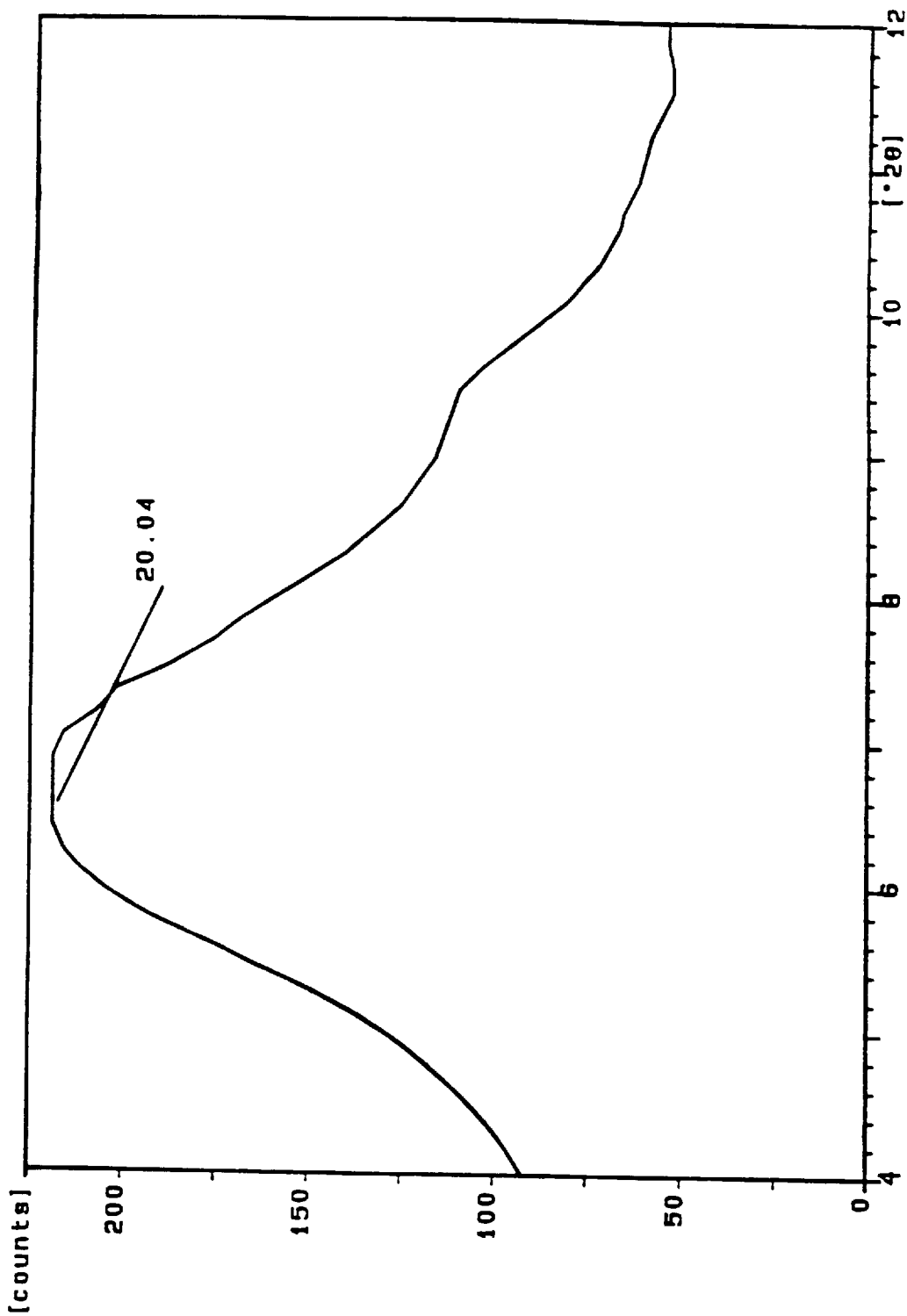
FIG. 5 is an x-ray diffraction pattern for a complex of PVA (weight average molecular weight of 15,000):sodium montmorillonite clay, in Angstroms, at a weight ratio of PVA:clay of 20:80.
Figure 6:
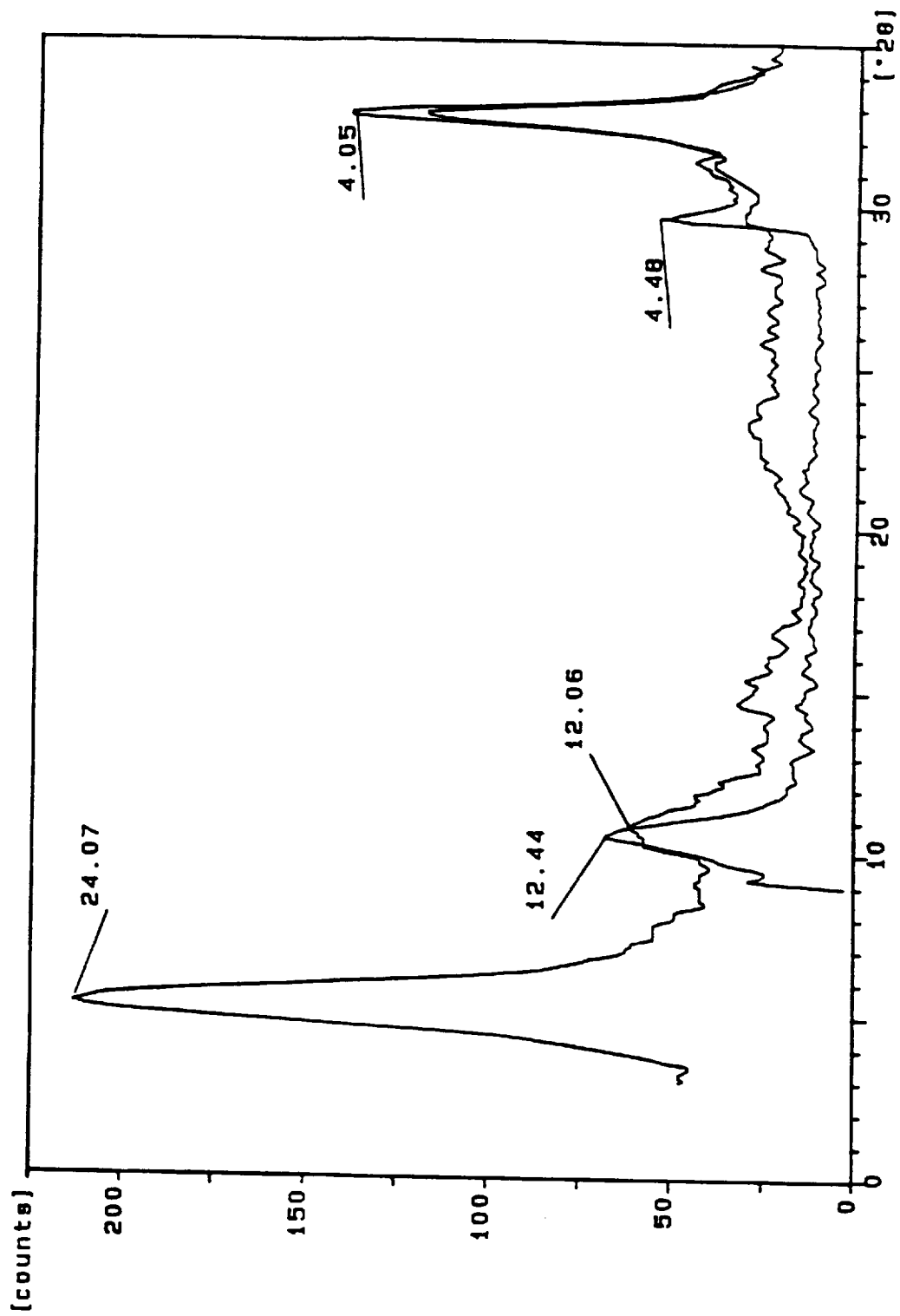
FIG. 6 is an x-ray diffraction pattern for a complex of PVP:sodium montmorillonite clay, in Angstroms, at a weight ratio of PVP:clay of 20:80 (upper pattern); and an x-ray diffraction pattern for 100% sodium montmorillonite clay having a crystobalite impurity (lower pattern)
Figure 7:
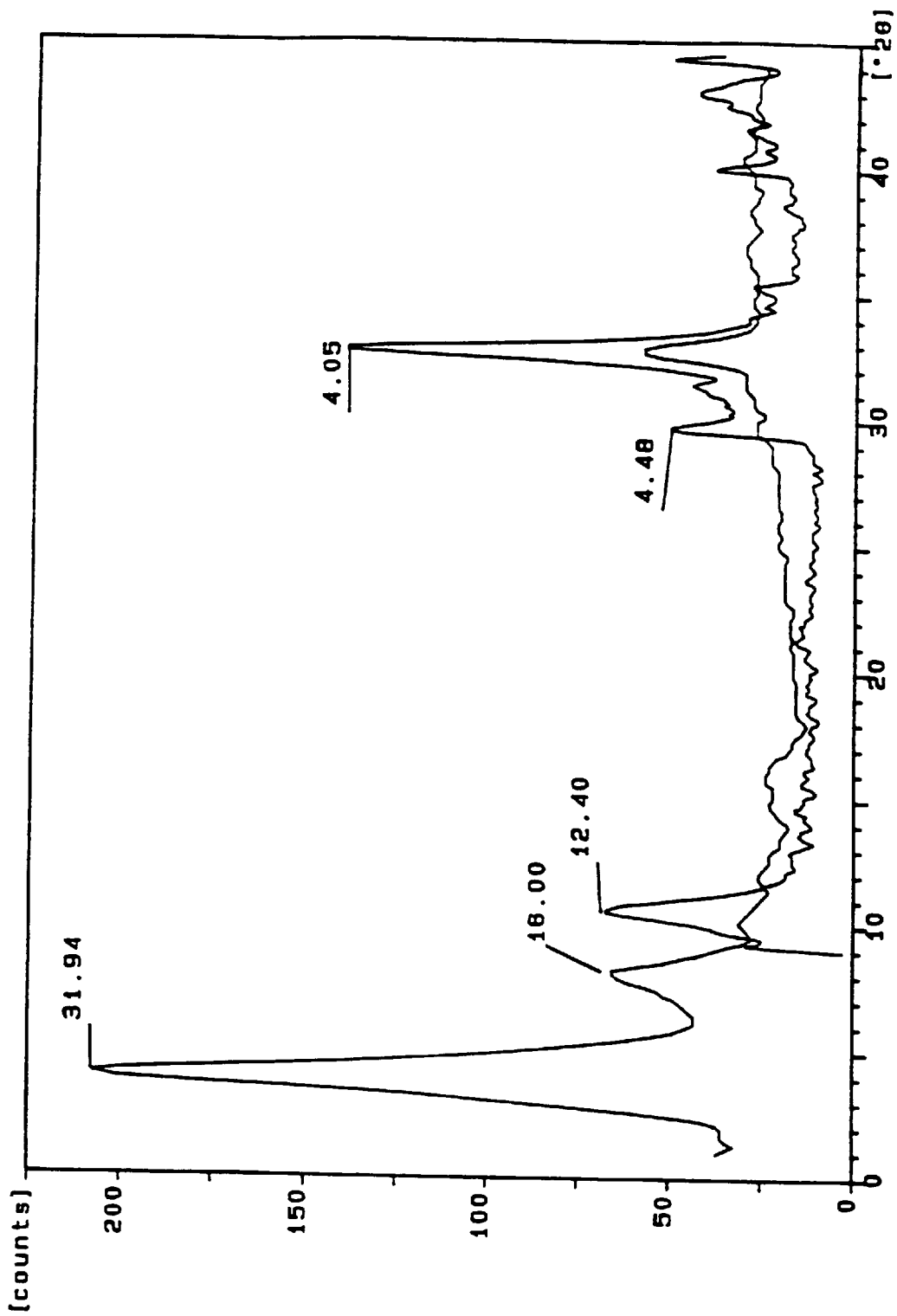
FIG. 7 is an x-ray diffraction pattern for a complex of PVP:sodium montmorillonite clay, in Angstroms, at a weight ratio of PVP:clay of 50:50 (upper pattern); and an x-ray diffraction pattern for ≈100% sodium montmorillonite clay having a crystobalite impurity (lower pattern)

The graphs of FIGS. 3 to 5 are x-ray diffraction patterns of blends of different water-soluble polymers with sodium bentonite clay. The pattern of FIGS. 3 and 4 are taken from intercalated clay 20% by weight polyvinylpyrrolidone (weight average molecular weight=10,000 for FIG. 3; 40,000 for FIG. 4) and 80% by weight sodium bentonite clay. The blends were formed by mixing the PVP and clay from a 2% solution of PVP and a 2% dispersion of sodium bentonite in a 1:4 ratio, respectively. As shown, the PVP-:clay complexed since no d(001) smectite peak appears at about 12.4 Å. Similar results are shown for 20% polyvinyl alcohol, 80% sodium bentonite, as shown in FIG. 5, blended in the same way and in the same ratio. The d(001) peak of non-exfoliated (layered) sodium bentonite clay appears at about 12.4 Å, as shown in the x-ray diffraction pattern for sodium bentonite clay (containing about 10% by weight water) in the lower x-ray diffraction patterns of FIGS. 6 and 7. The graphs of FIG. 6 are x-ray diffraction patterns of sodium bentonite clay (montmorillonite) and a PVP:clay complex that was obtained by extrusion of a blend of 20% by weight polyvinylpyrrolidone (molecular weight 10,000) and 80% sodium bentonite clay (containing a crystobalite impurity, having a d-spacing of about 4.05 Å) with 35% water by weight of dry clay. As shown in FIG. 6, the PVP clay complexed since no d(001) smectite peak appears at about 12.4 Å. There are basal spacings with a d(001) peak of PVP:clay complex at about 24 Å and d(002) peak of PVP:clay complex at about 12 Å, that shows close to regular structure of this intercalated composite with a PVP-:clay ratio equal to 1:4. The graphs of FIG. 7 are x-ray diffraction patterns of sodium bentonite clay (montmorillonite) and PVP:clay complex that was obtained by extrusion of blend of 50% by weight polyvinylpyrrolidone (molecular weight 10,000) and 50% of sodium bentonite clay (containing a crystobalite impurity, having d-spacing of about 4.05 Å) with 35% water by weight of dry clay. As shown in FIG. 7, the PVP:clay complexed since no d(001) smectite peak appears at about 12.4 Å. There are basal spacings with a d(001) peak of the PVP:clay complex at about 32 Å and a d(002) peak of PVP:clay complex at about 16 Å that shows close to regular structure of this intercalated composite with a PVP:clay ratio equal to 1:1. When mechanical blends of powdered sodium bentonite clay (containing about 10% by weight water) and powdered polyvinylpyrrolidone (PVP) polymer were mixed with water (about 75% by weight water), the polymer was intercalated between the bentonite clay platelets, and an exothermic reaction occurred that, it is theorized, resulted from the polymer being bonded to the internal faces of the clay platelets sufficiently for exfoliation of the intercalated clay.

It should be noted, also, that exfoliation did not occur unless the bentonite clay included water in an amount of at least about 4% by weight, based on the dry weight of the clay, preferably about 10% to about 15% water. The water can be included in the clay as received, or can be added to the clay prior to or during polymer contact.

It should also be noted that the exfoliation occurred without shearing—the layered clay exfoliated naturally after sufficient intercalation of polymer between the platelets of the layered bentonite—whether the intercalate was achieved by using sufficient water, e.g., about 20% to about 80% by weight, based on the dry weight of the clay, for sufficient migration of the polymer into the interlayer spaces, and preferably also extruding; or by heating the blends to at least the intercalant polymer melt temperature, while the clay includes at least about 5% by weight water, for polymer intercalation.

Figure 8:
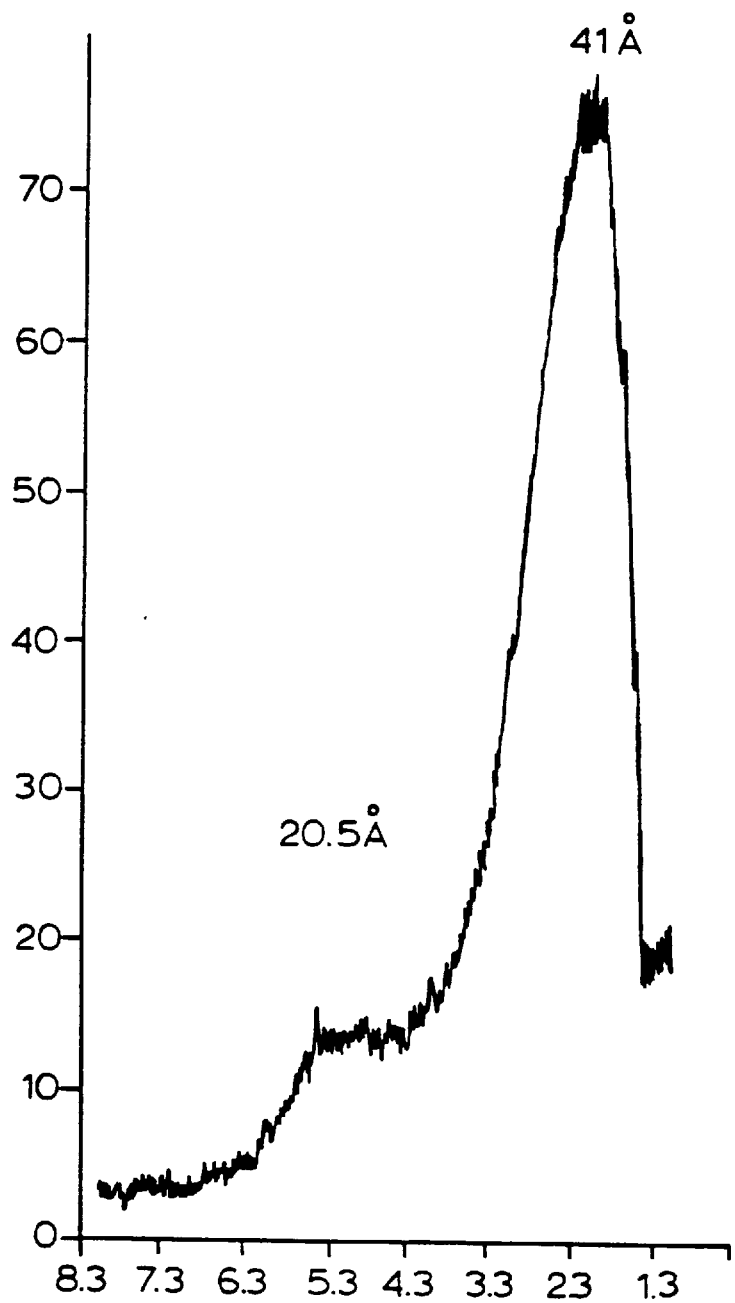
FIG. 8 is a portion of an x-ray diffraction pattern for PVP:sodium montmorillonite clay, in Angstroms, at a PVP:clay ratio of 80:20, showing a PVP:clay complex peak or d(001) spacing of about 41 Å.

The x-ray diffraction pattern of FIG. 8 shows that at a ratio of 80% PVP, 20% clay, the periodicity of the intercalated composite with PVP clay ratio equal to 4:1 is increased to about 41 Å.

EXAMPLE 3

Figure 9:
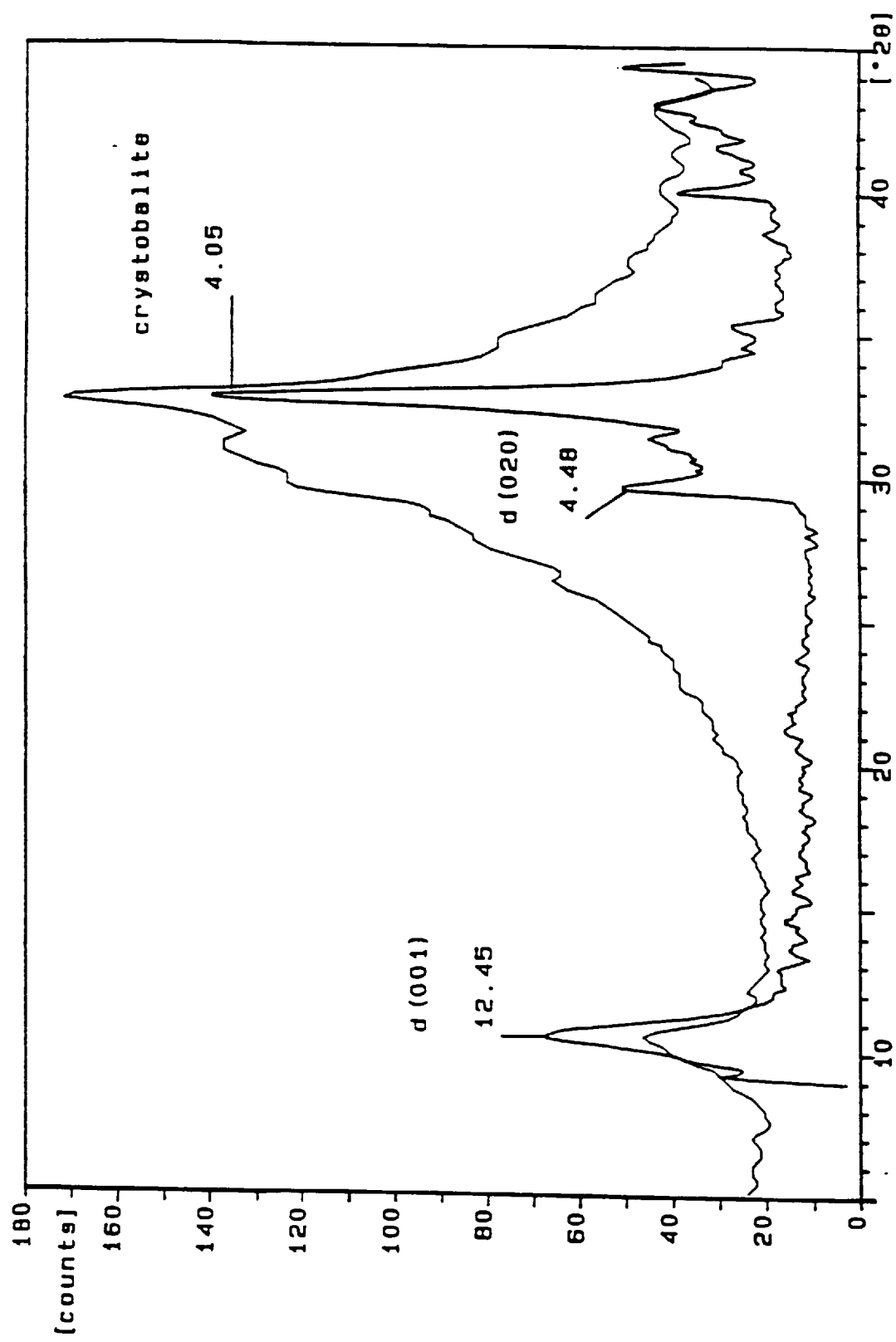
FIG. 9 is an x-ray diffraction pattern for a mechanical blend of a polyamide and a dry (about 8% by weight moisture) sodium montmorillonite clay in a weight ratio of 80 polyamide:20 sodium montmorillonite clay (upper pattern); and≈100% sodium montmorillonite clay, with a crystobalite impurity, (lower pattern), showing characteristic smectite clay d(001) peaks at about 12.4 Å, d(020) smectite clay peaks at about 4.48 Å; and a crystobalite impurity peak at about 4.05 Å for both upper and lower patterns.

The upper x-ray diffraction pattern shown in FIG. 9 was taken on a mechanical blend of 80% by weight polyamide and 20% by weight sodium bentonite clay. The lower x-ray diffraction pattern was taken on 100% sodium bentonite clay. The polyamide was not intercalated between the clay platelets since the blend was dry (clay contained about 8% by weight water) and the polyamide was not melted. As shown in FIG. 1, both diffraction patterns show the characteristic d(001) 12.45 Å and the d(020) 4.48 Å peaks characteristic of non-exfoliated smectite clays and a 4.05 Å peak characteristic of a crystobalite impurity.

Figure 10:
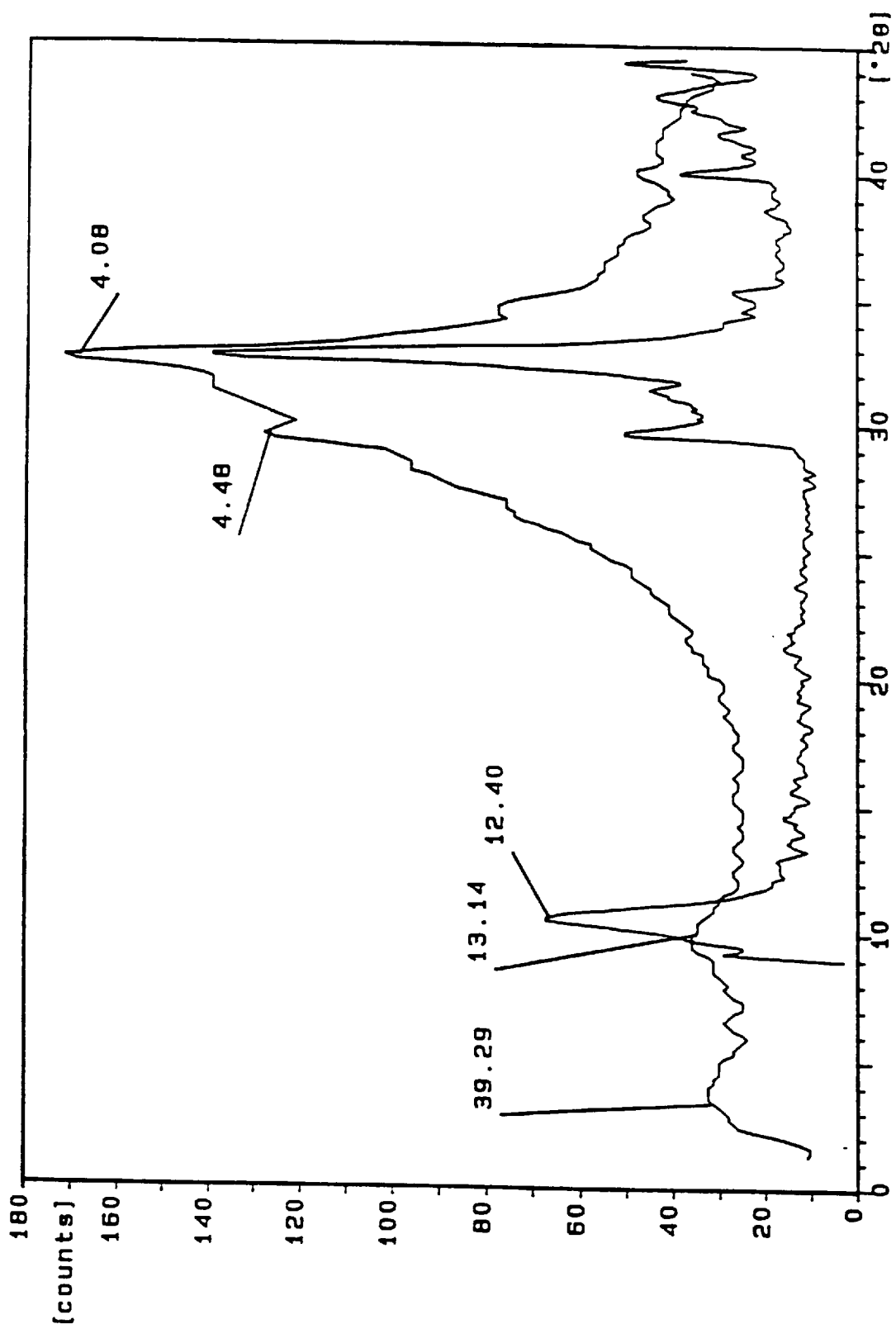
FIG. 10 is an x-ray diffraction pattern for the mechanical blend shown in the upper pattern (80 polyamide:20 sodium montmorillonite clay) of FIG. 9, after heating the mechanical blend to the melt temperature of the polyamide (upper pattern) to achieve intercalation and exfoliation, in comparison to the x-ray diffraction pattern for≈100% sodium montmorillonite clay, having a crystobalite impurity, (lower pattern), showing the disappearance of the characteristic smectite clay d(001) peak at about 12.4 Å; the d(020) peak at about 4.48 Å, characteristic of single smectite platelets; and a characteristic crystobalite impurity peak at about 4.08 Å (upper pattern)

As shown in FIG. 10, when the 80% polyamide, 20% sodium bentonite mechanical blend was heated to the polyamide melt temperature, and preferably at least about 40°–50° C. above, the polymer melt temperature for faster intercalation, e.g., 230° C., (see the upper x-ray diffraction pattern for the melt) the smectite d(001) peak at 12.45 Å was no longer present, since the polyamide was intercalated between the clay platelets and the platelets were exfoliated, thereby eliminating the d(001) periodicity characteristic of aligned smectite platelets. The mechanical blend was melted by heating the blend to the melt temperature under a $N_2$ head space to avoid oxidation. The lower x-ray diffraction pattern in FIG. 10 again is the 100% sodium bentonite pattern for comparison.

Alternatively, the mechanical blend could be blended with about 10% by weight, preferably about 20% to about 50% by weight water or organic solvent, based on the total weight of the blend, and extruded to achieve intercalation and exfoliation.

EXAMPLE 4

Figure 11:
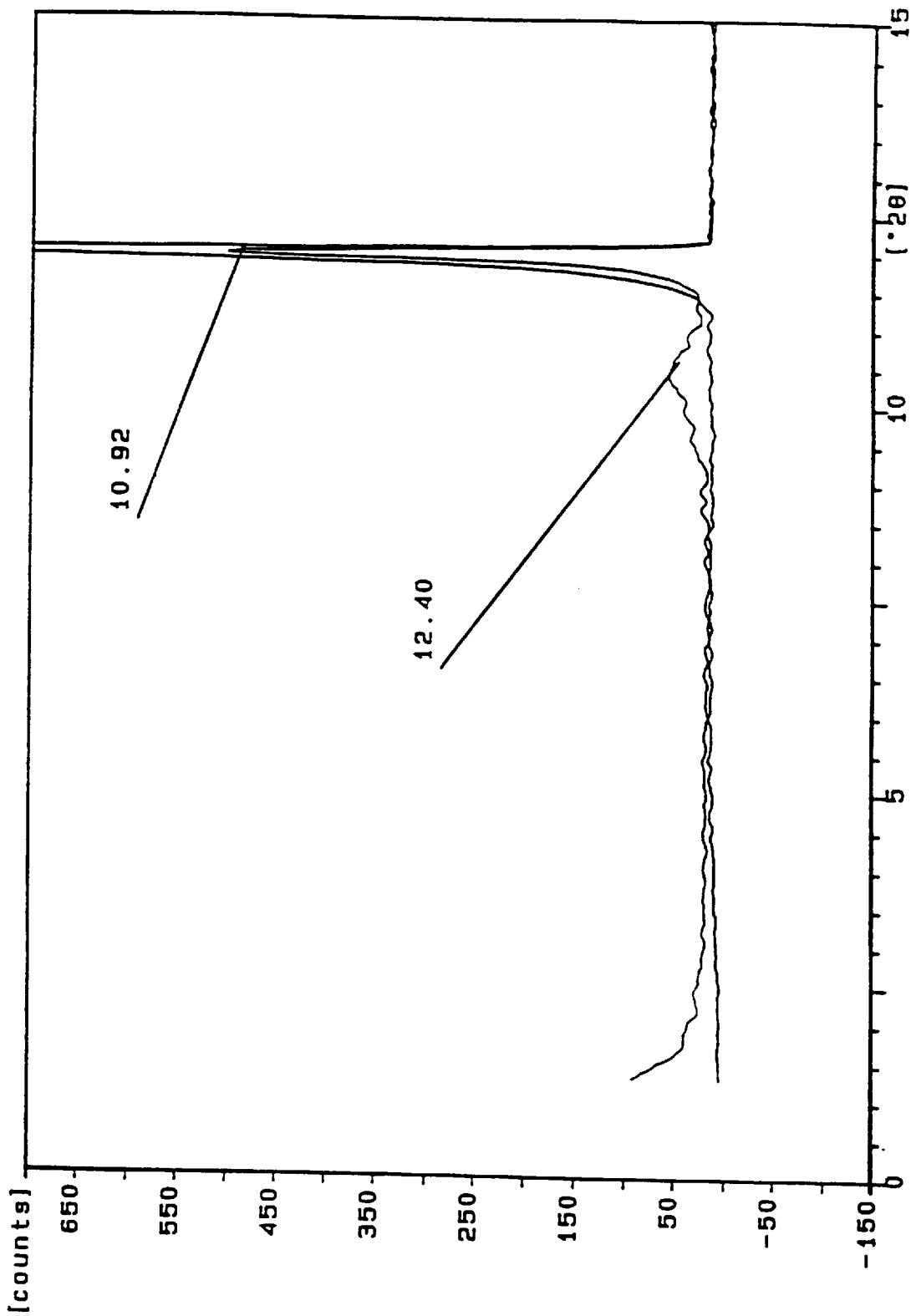
FIG. 11 is an x-ray diffraction pattern similar to FIG. 9, showing a mechanical blend of dimethylterephthalate (DMTPh) (70% by weight) and dry (about 8% moisture) sodium montmorillonite clay (30% by weight), on a smaller scale than FIG. 1, showing a characteristic smectite clay d(001) peak at about 12.4 Å for the mechanical blend; and an x-ray diffraction pattern for 100% DMTPh.
Figure 12:
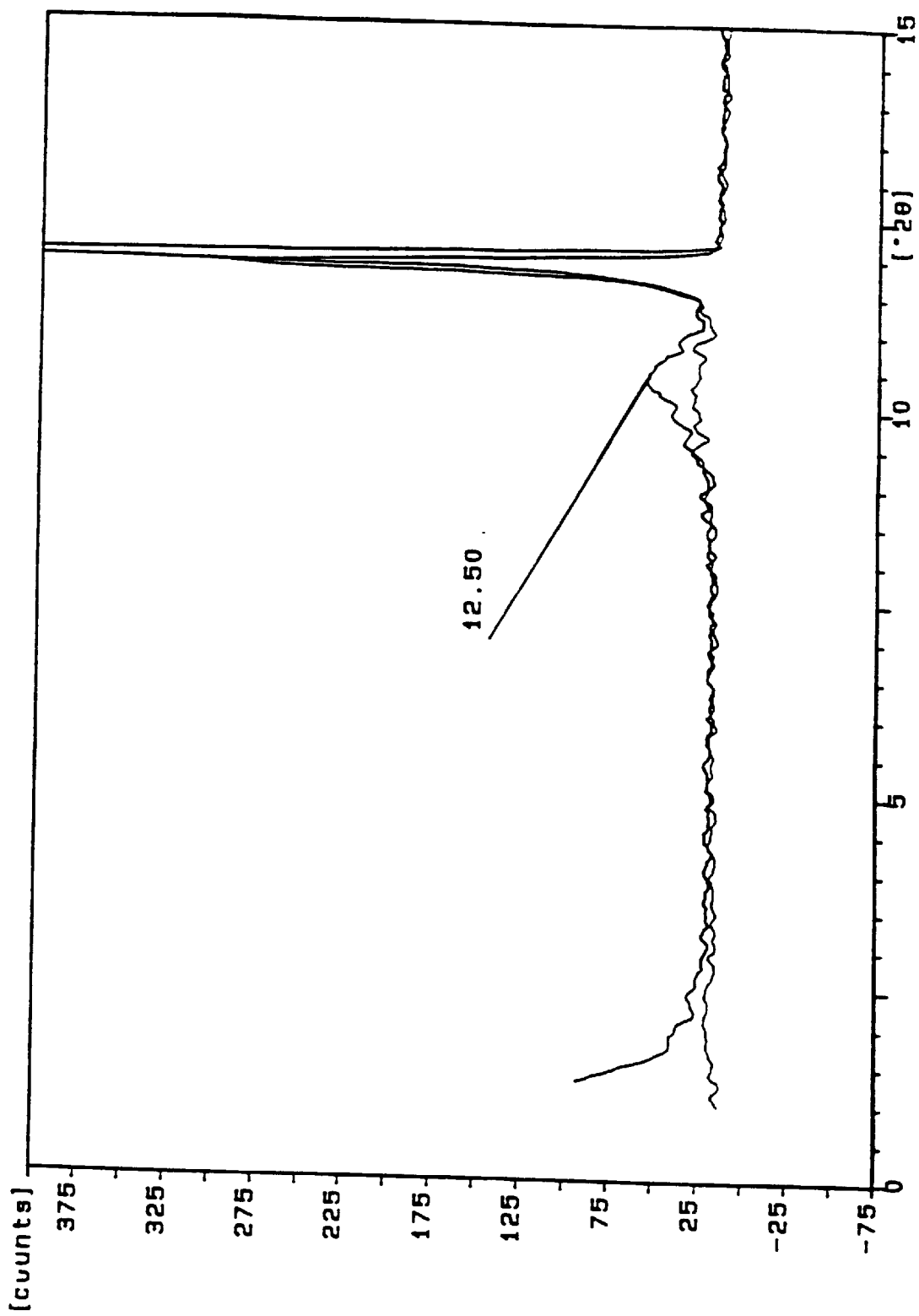
FIG. 12 is an x-ray diffraction pattern for the 70:30 mechanical blend of DMTPh:clay shown in FIG. 11, after heating the blend to above the melt temperature of the DMTPh (about 230° C.), showing the disappearance of the characteristic smectite clay d(001) peak (about 12.4 Å) for the melt, showing exfoliation, and a DMTPh:clay complex (intercalate) peak at about 12.5 Å; and an x-ray diffraction pattern for 100% DMTPh.

Similar to FIG. 9, the x-ray diffraction pattern shown in FIG. 11 was taken from a mechanical blend of 70% by weight dimethylterephthalate and 30% by weight sodium bentonite clay. Because of the different scales of FIG. 3 versus FIG. 9, the d(001) smectite peak at about 12.4 Å is not as high. The lower x-ray diffraction pattern of FIG. 11 is from 100% dimethylterephthalate. As shown in FIG. 12, when the mechanical blend was subjected to a temperature above the dimethylterephthalate melt temperature, about 230° C., the d(001) 12.4 Å smectite peak disappeared since the clay was intercalated with the polymer and exfoliated (lower pattern), while it appears for the mechanical blend (upper pattern).

EXAMPLE 5

Figure 13:
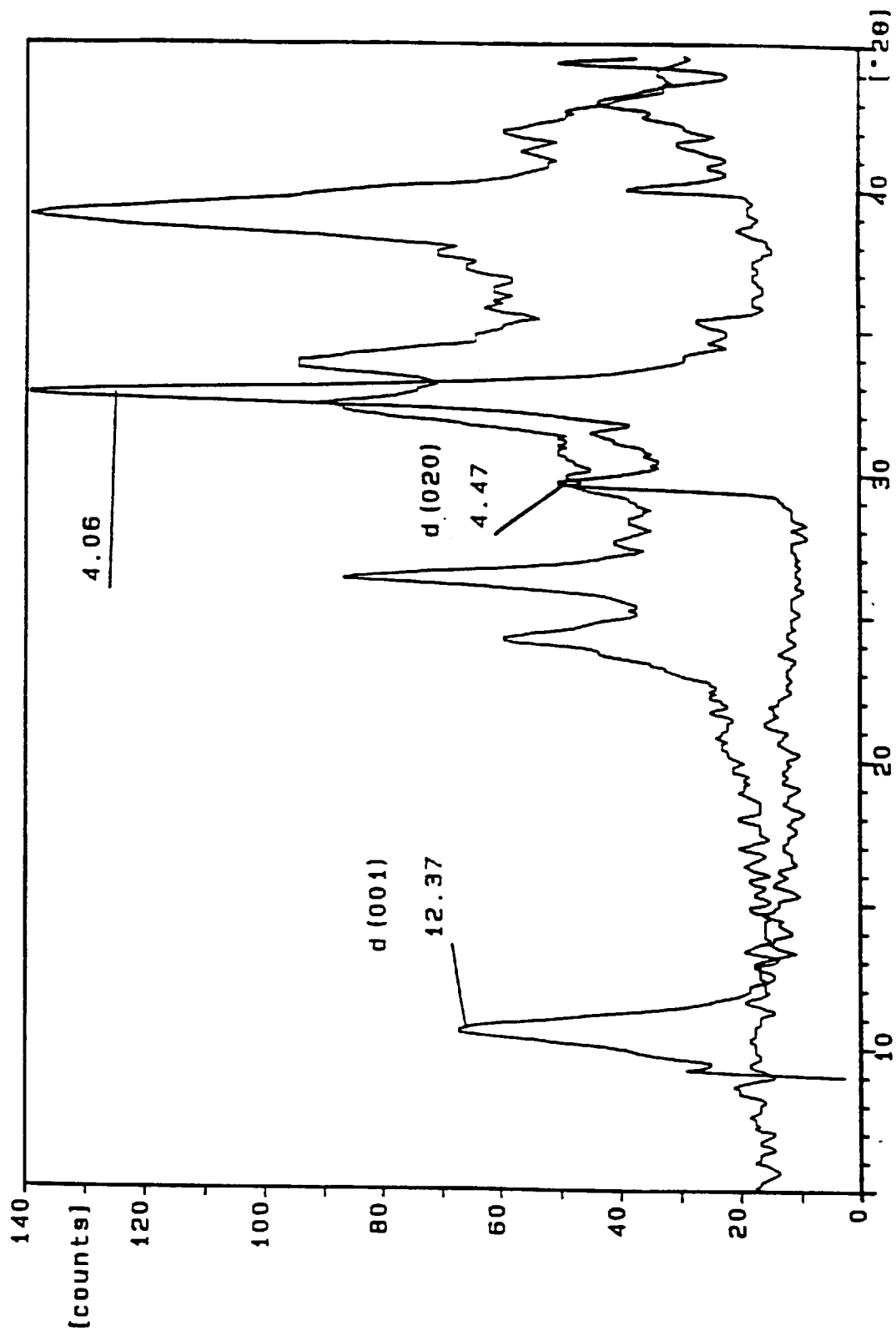
FIG. 13 is an x-ray diffraction pattern for a 230° C. melt (complex) of polyethyleneterephthalate (PET):sodium montmorillonite clay at a weight ratio of PET:clay of 90:10 (upper pattern) showing the disappearance of the characteristic smectite d(001) peak at about 12.4 Å for the melt, showing exfoliation; and an x-ray diffraction pattern for 100%.t sodium bentonite, having a crystobalite impurity, (lower pattern)

The upper x-ray diffraction pattern of FIG. 13 was taken from a melt of 90% by weight polyethylene terephthalate (PET) and 10% by weight sodium bentonite clay (containing about 8% by weight moisture). The lower pattern was taken from 100% sodium bentonite, showing the characteristic smectite d(001) peak at about 12.4 (12.37) Å, and the characteristic d(020) peak at 4.47 A. When heated to the PET melt temperature (upper x-ray diffraction pattern), the d(001) smectite peak disappeared since the PET was intercalated between the clay platelets and the platelets were exfoliated.

EXAMPLE 6

Figure 14:
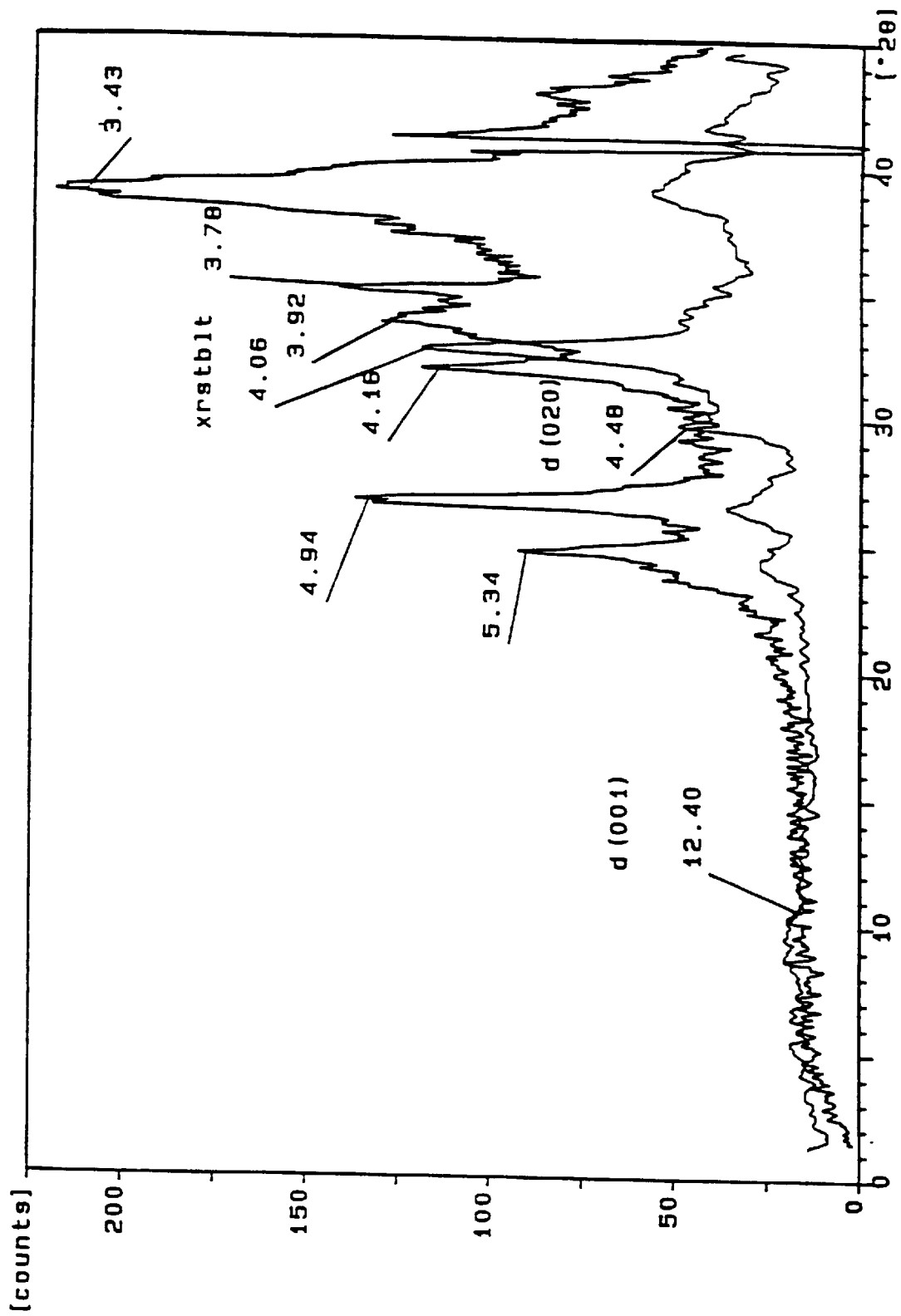
FIG. 14 is an x-ray diffraction pattern for a 250° C. melt (complex) of hydroxyethylterephthalate (HETPh):sodium montmorillonite clay at a weight ratio of HETPh:clay of 60:40 (lower pattern) showing the disappearance of the characteristic smectite d(001) peak at about 12.4 Å for the melt, showing exfoliation; and an x-ray diffraction pattern for 100% HETPh (upper pattern)

FIG. 14 shows x-ray diffraction patterns from a melted (250° C.) blend of 60% by weight hydroxyethylterephthalate (HETPh) and 40% by weight sodium bentonite (containing about 8% by weight moisture), for the lower pattern, and 100% HETPh for the upper pattern. As shown, no characteristic smectite d(001) peak appears at about 12.4 Å for the melted blend while there is the characteristic d(020) peak at about 4.48 Å, indicating that the clay was intercalated with the HETPh, and the platelets were exfoliated.

EXAMPLE 7

Figure 15:
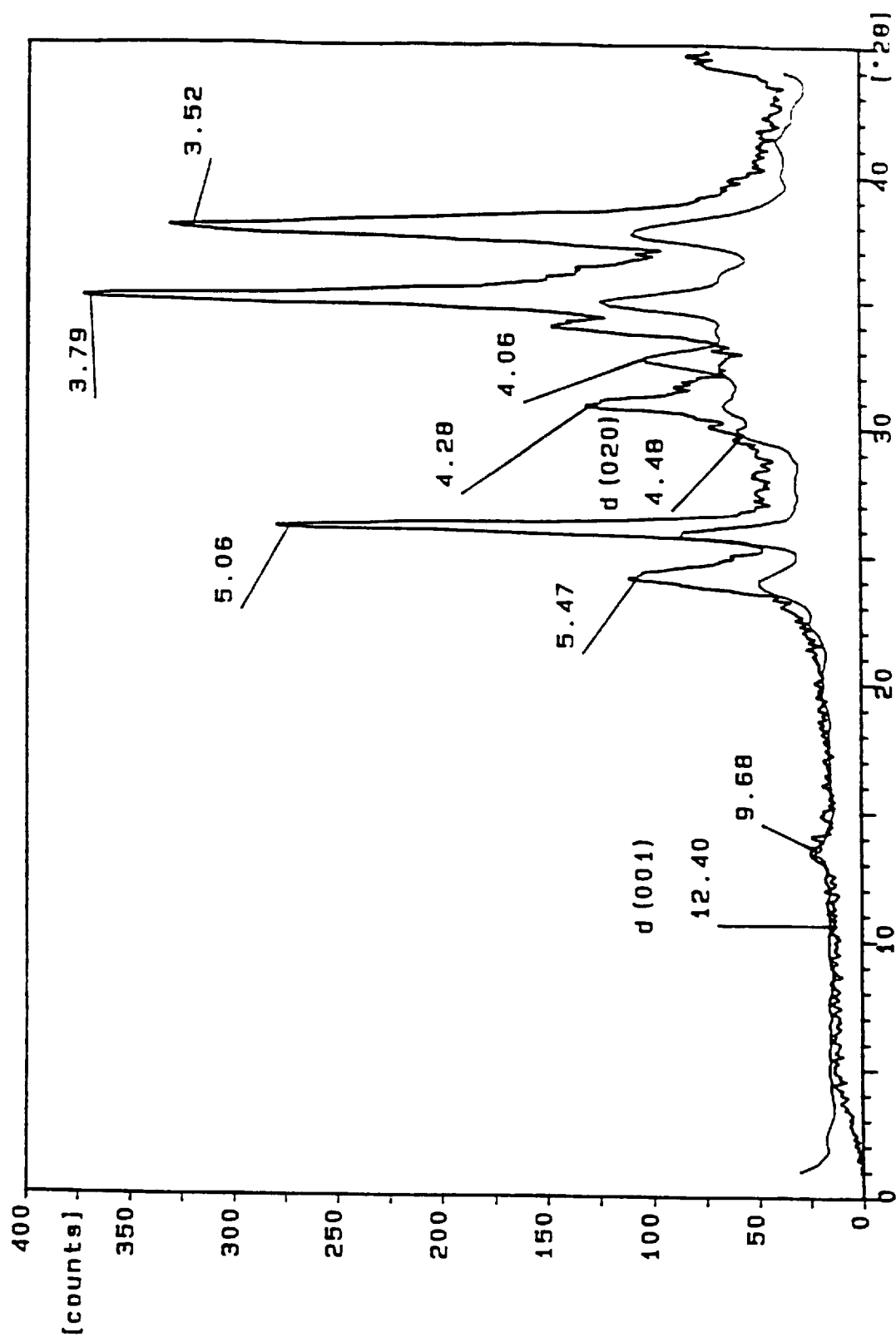
FIG. 15 is an x-ray diffraction pattern for 250° C. melt (complex) of hydroxybutylterephthalate (HBTPh):sodium montmorillonite clay at a weight ratio of HBTPh:clay of 70:30 (lower pattern) showing the disappearance of the characteristic smectite d(001) peak at about 12.4 Å for the melt, showing exfoliation; and an x-ray diffraction pattern for 100% HBTPh (lower pattern)

FIG. 15 shows x-ray diffraction patterns from a melted (250° C.) blend of 70% by weight hydroxybutylterephthalate (HBTPh) and 30% sodium bentonite (containing about 8% by weight moisture). As shown, no characteristic smectite d(001) peak appears at about 12.4 Å for the melted blend, indicating that the clay was intercalated with the HBTPh, and the platelets were exfoliated.

EXAMPLE 8

Figure 16:
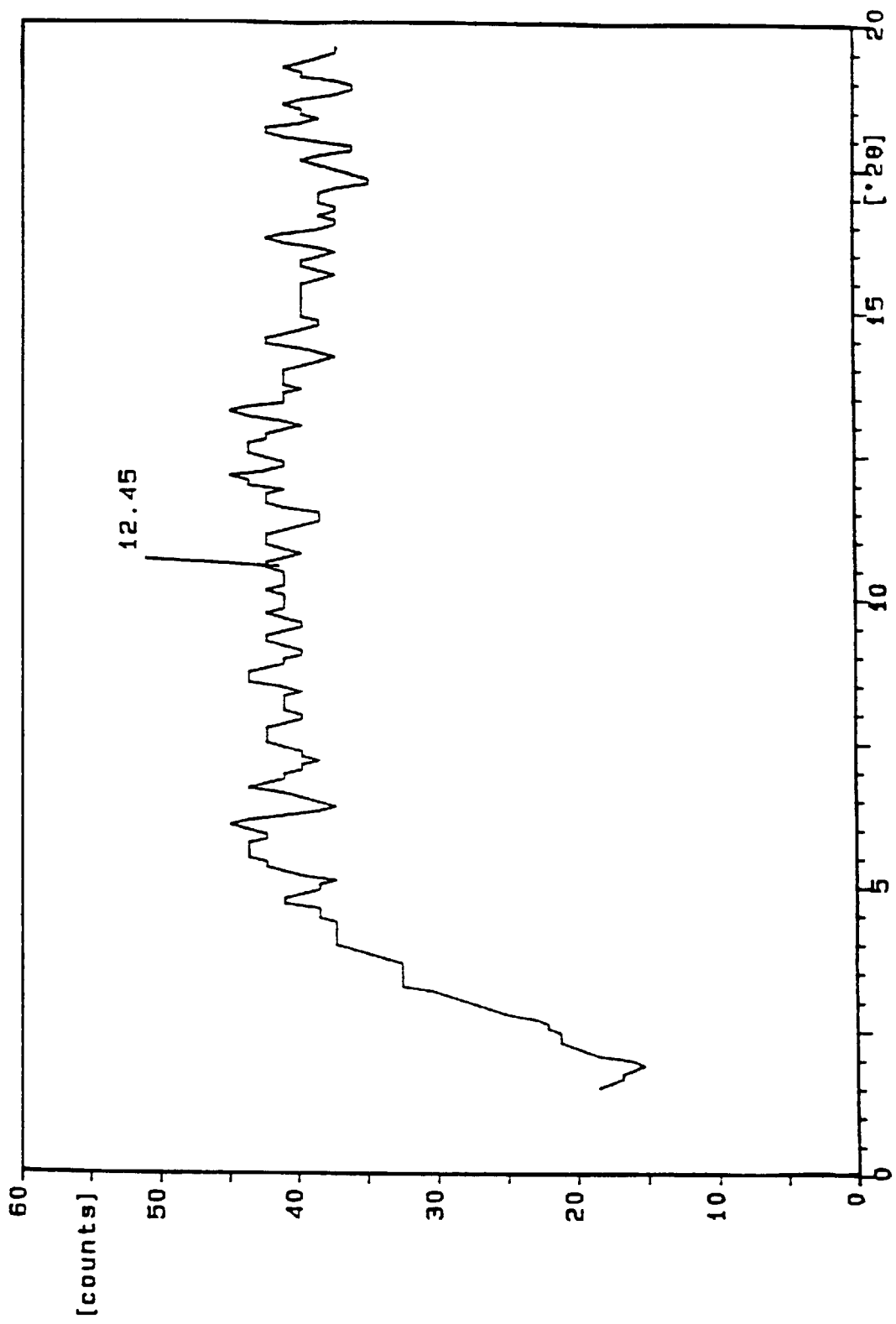
FIG. 16 is an x-ray diffraction pattern for a polycarbonate:sodium montmorillonite clay complex at a melted blend (280° C.) ratio of polycarbonate:clay of 50:50, showing the disappearance of the characteristic smectite d(001) peak at about 12.4 Å for the melt, showing exfoliation.
Figure 17:
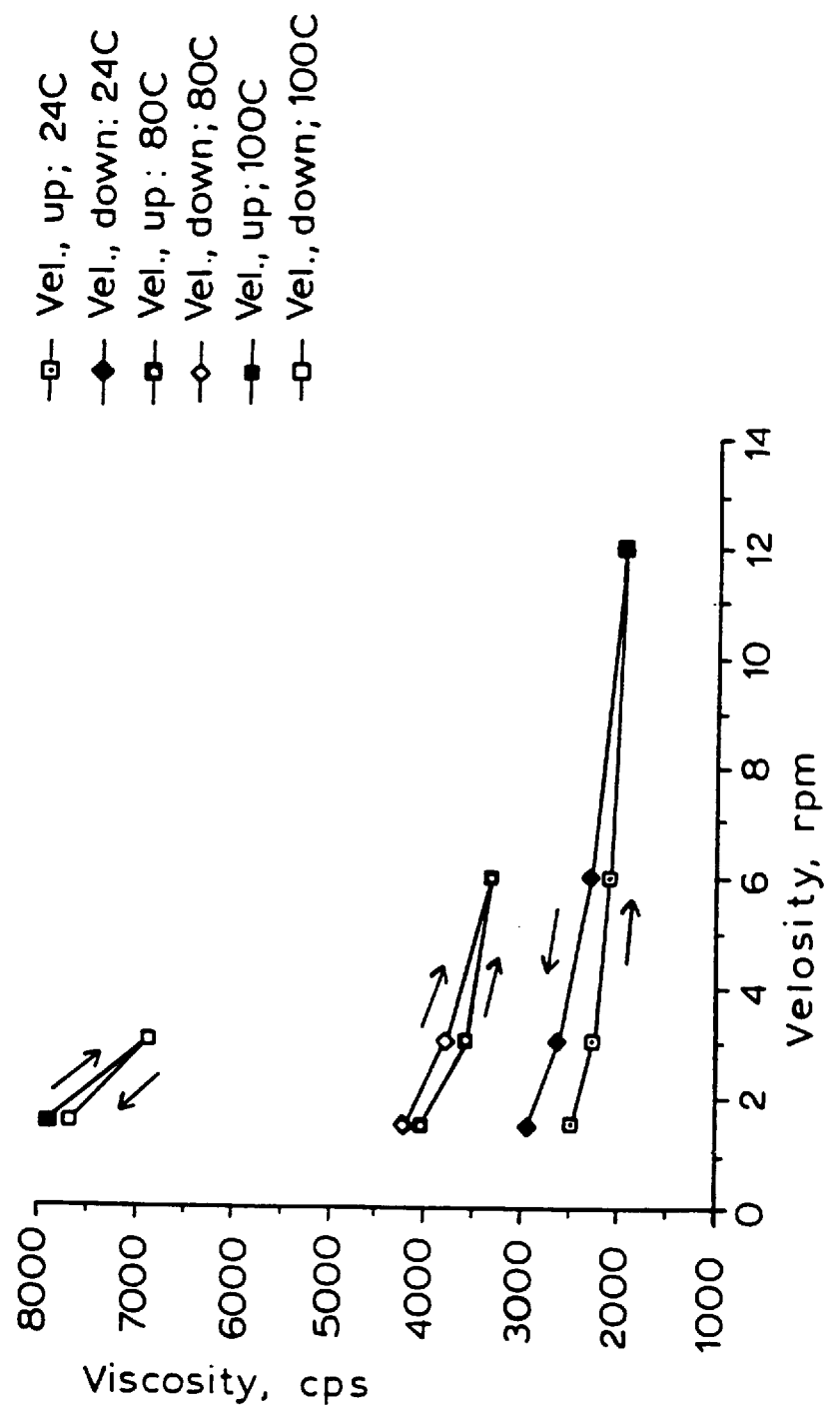
FIG. 17 is a graph of composition viscosity at 24° C. vs. spindle velosity r.p.m. for compositions of 10% by weight Na bentonite clay: polyvinylpyrrolidone (PVP) complex, 6% by weight water, and 84% by weight glycerol showing thixotropy at increased and decreased shear, and increased viscosity with increased temperatures of intercalation in formation of the clay:PVP complex.
Figure 18:
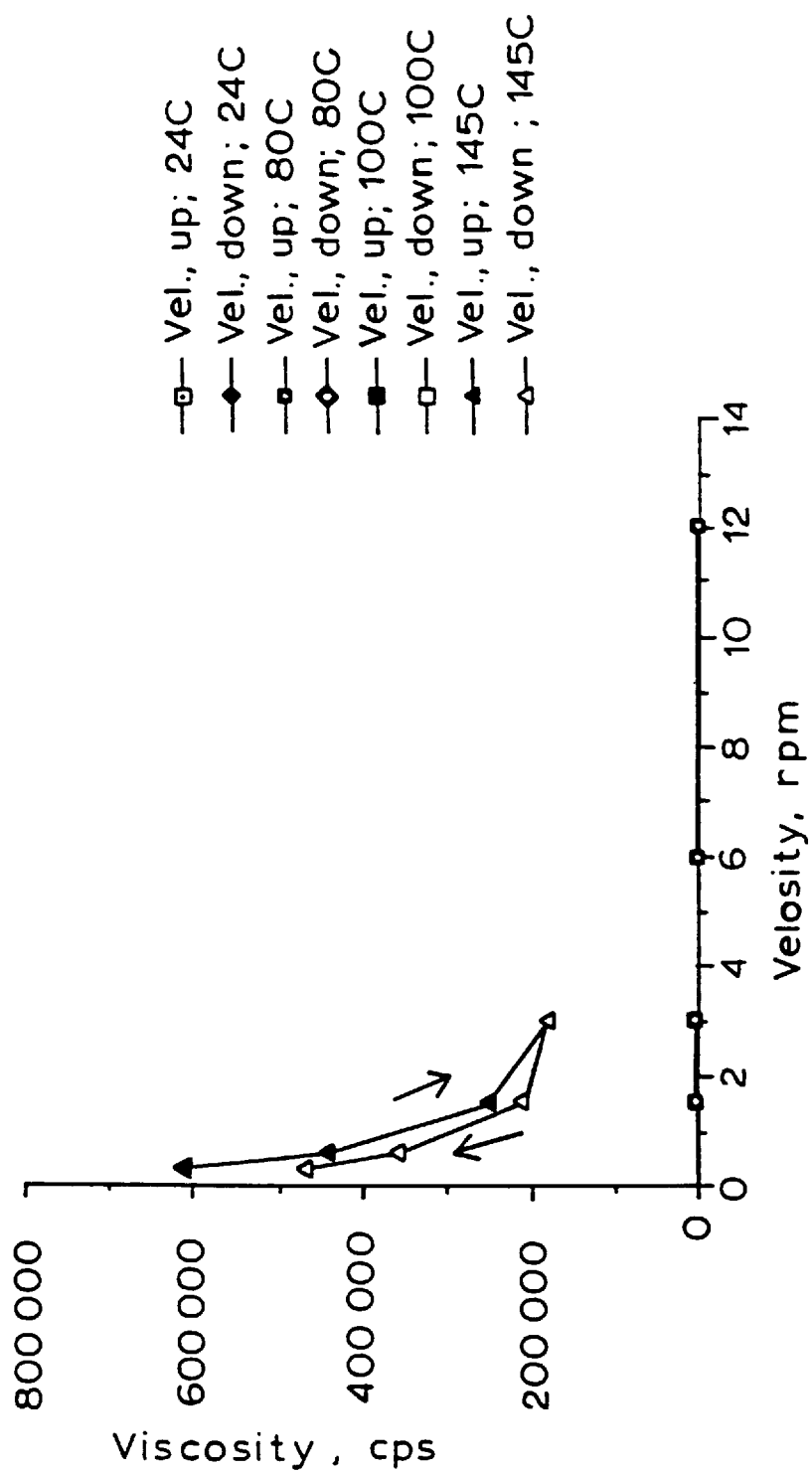
FIG. 18 is a graph similar to the graph of FIG. 17, at a different scale, showing the data from FIG. 17 along the horizontal axis, and showing an unexpected increase in viscosity achieved by heating the composition gel to a temperature of 145° C. before cooling and increasing viscosity at 24° C.
Figure 19:
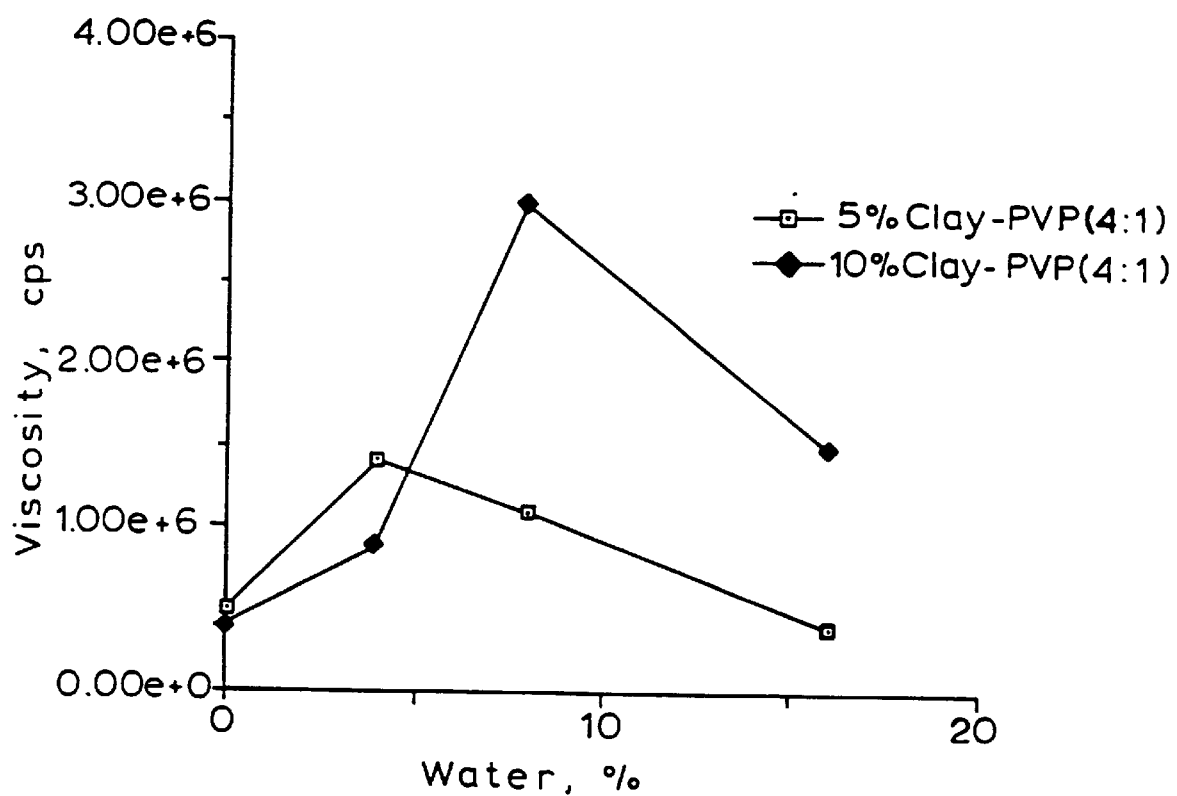
FIG. 19 is a graph of composition viscosity at 24° C. of compositions containing 5% clay:PVP complex and 10% by weight Na bentonite:PVP complex (4:1 weight ratio for both) mixed with water and glycerol with various amounts of water (water plus glycerol equals 100%) showing an increase in viscosity from about 500,000 centipoises to about 3,000,000 centipoises by increasing the water content from 0% (100% glycerol) to about 7.5% water, and a decrease in viscosity with the addition of more than 7.5% water.
Figure 20:
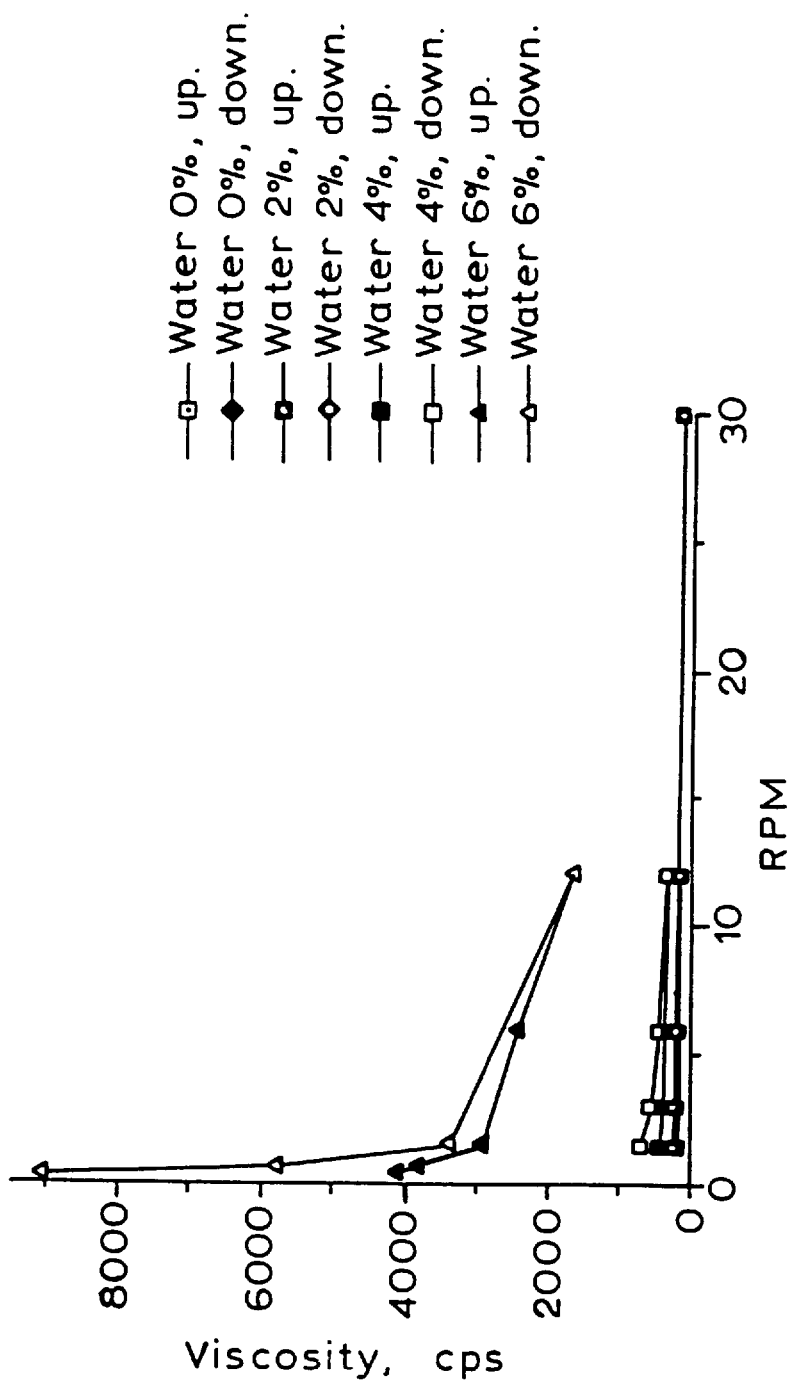
FIGS. 20 and 21 are graphs, at different scales, of composition viscosity at 24° C. of compositions containing 5% by weight Na bentonite clay: PVP complex (4:1 weight ratio); 0–6% by weight water; and 89–95% by weight ethylene glycol showing thixotropy with raising and lowering of shear (RPM) and an increase in viscosity with increased water content from 0% water to 2% water, 4% water and 6% water; and substantial increase in viscosity when the gel is heated to 85° C. before cooling to 24° C. to measure viscosity (FIG. 21)
Figure 21:
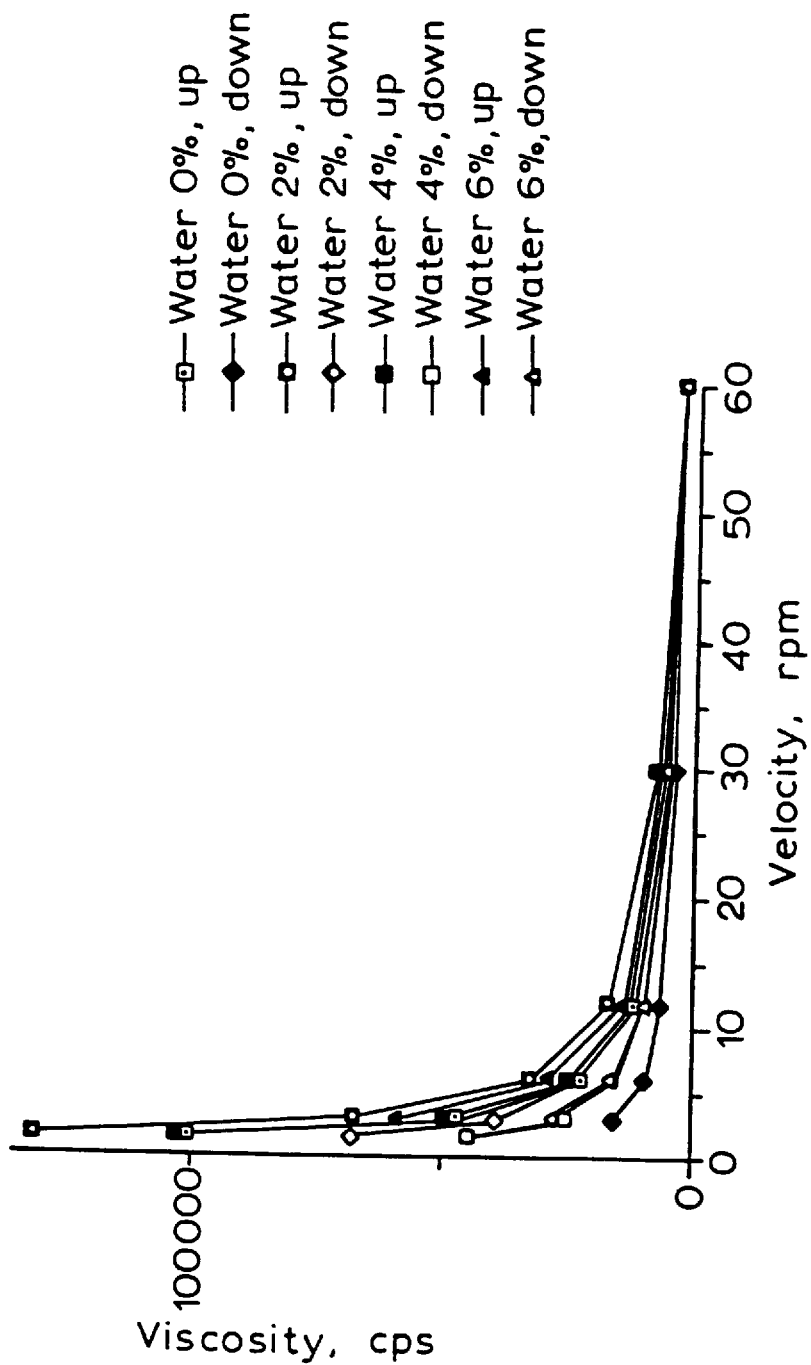
Figure 22:
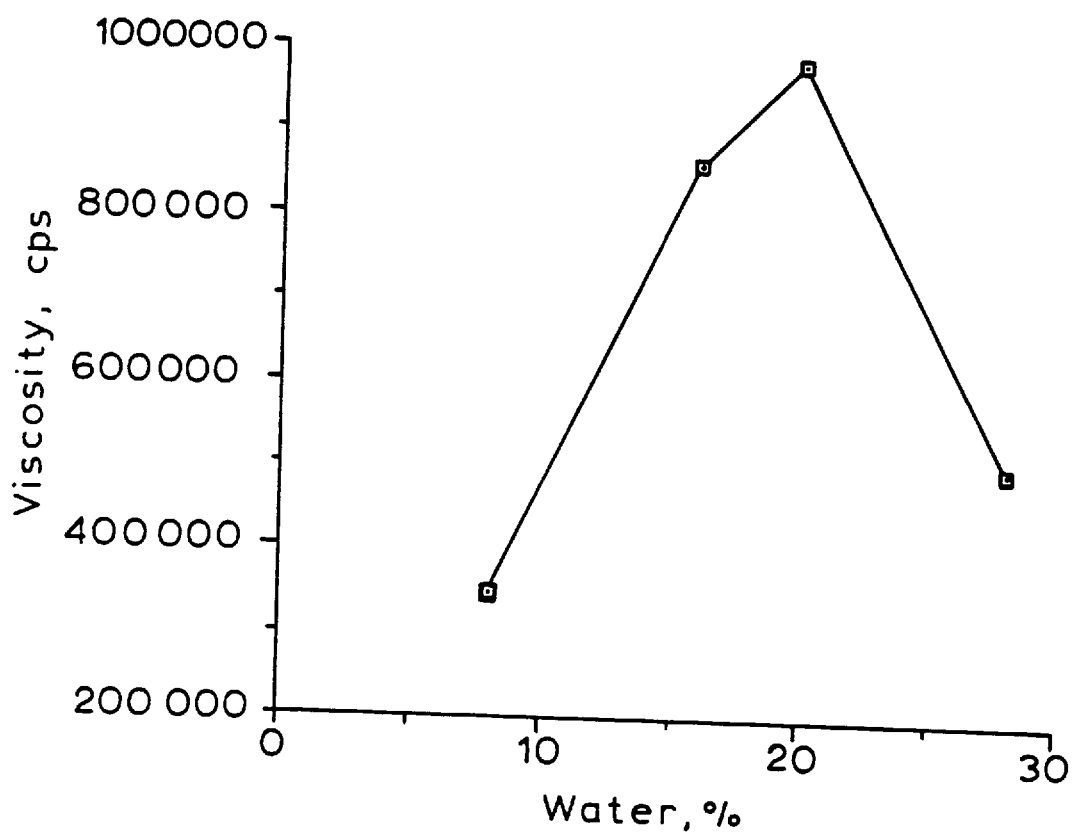
FIG. 22 is a graph of composition viscosity at 24° C. of compositions containing 10% by weight Na bentonite:PVP complex (4:1 weight ratio) mixed with water at about 8% to about 28% water and about 72% by weight to about 92% by weight ethanol (water plus ethanol=100%) showing an increase in viscosity with added water between about 8% water and about 20% water by weight and a decrease in viscosity with more than about 20% by weight water.
Figure 23:
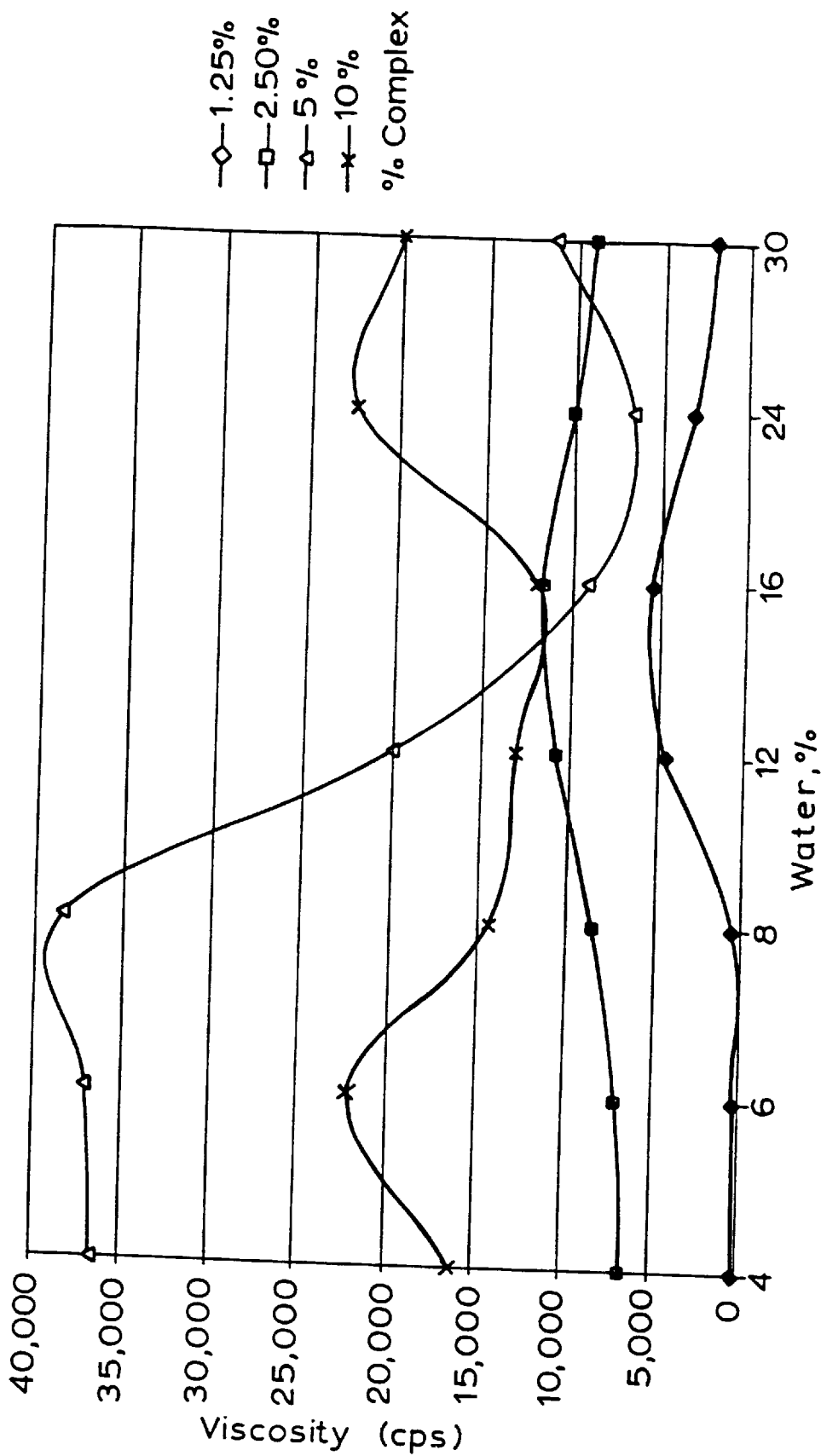
FIGS. 23 and 24 are graphs of composition viscosity at 24° C. of compositions of varied percentages of water and propylene glycol at various loadings between about 1.25% by weight and about 10% by weight of a complex of Na bentonite clay:PVP (4:1 clay:PVP weight ratio) showing the change in viscosity at various $H_2O$ percentages ($H_2O$ plus propylene glycol =100%) and at various clay:PVP complex loadings.
Figure 24:
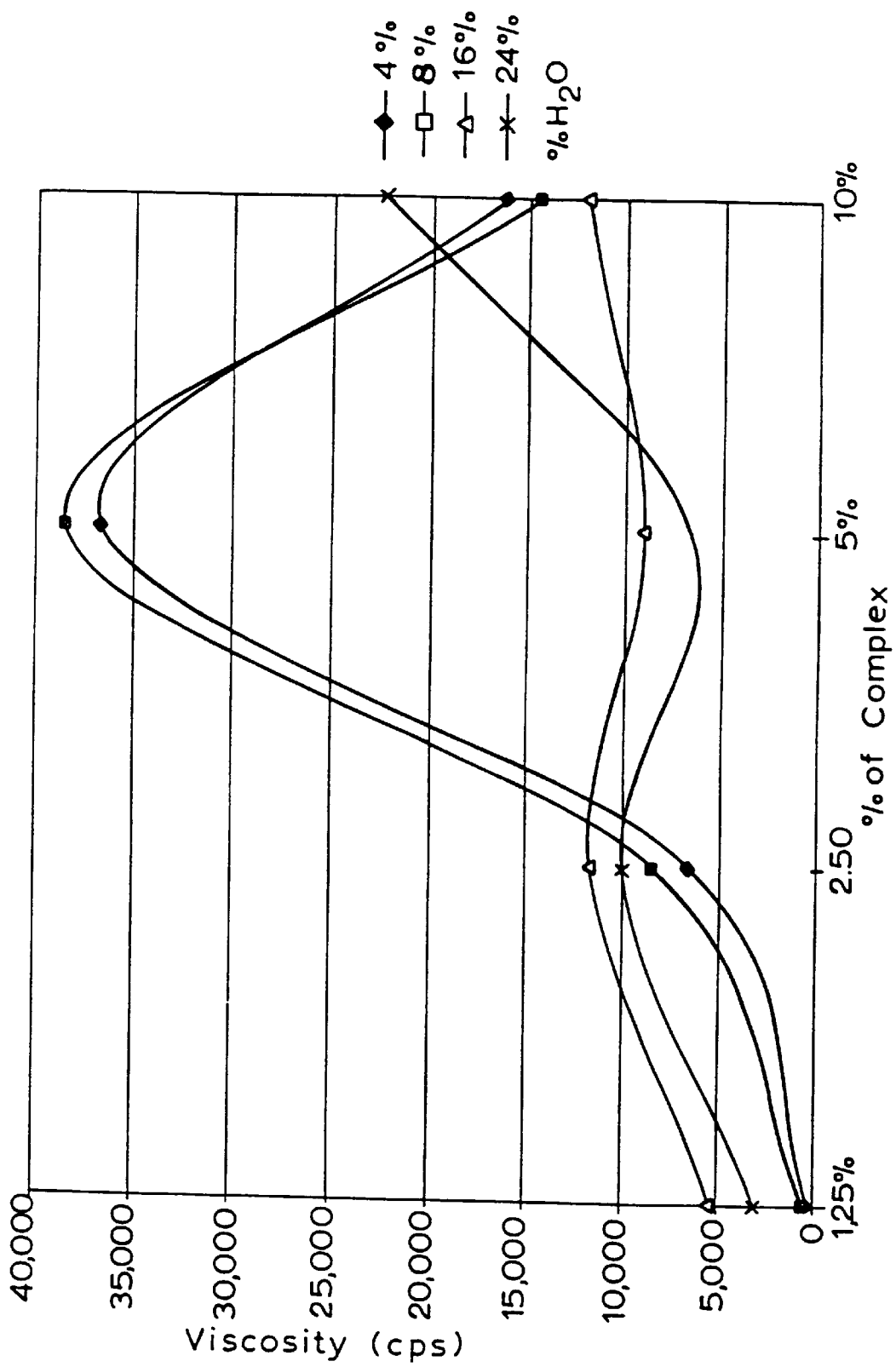
Figure 25:
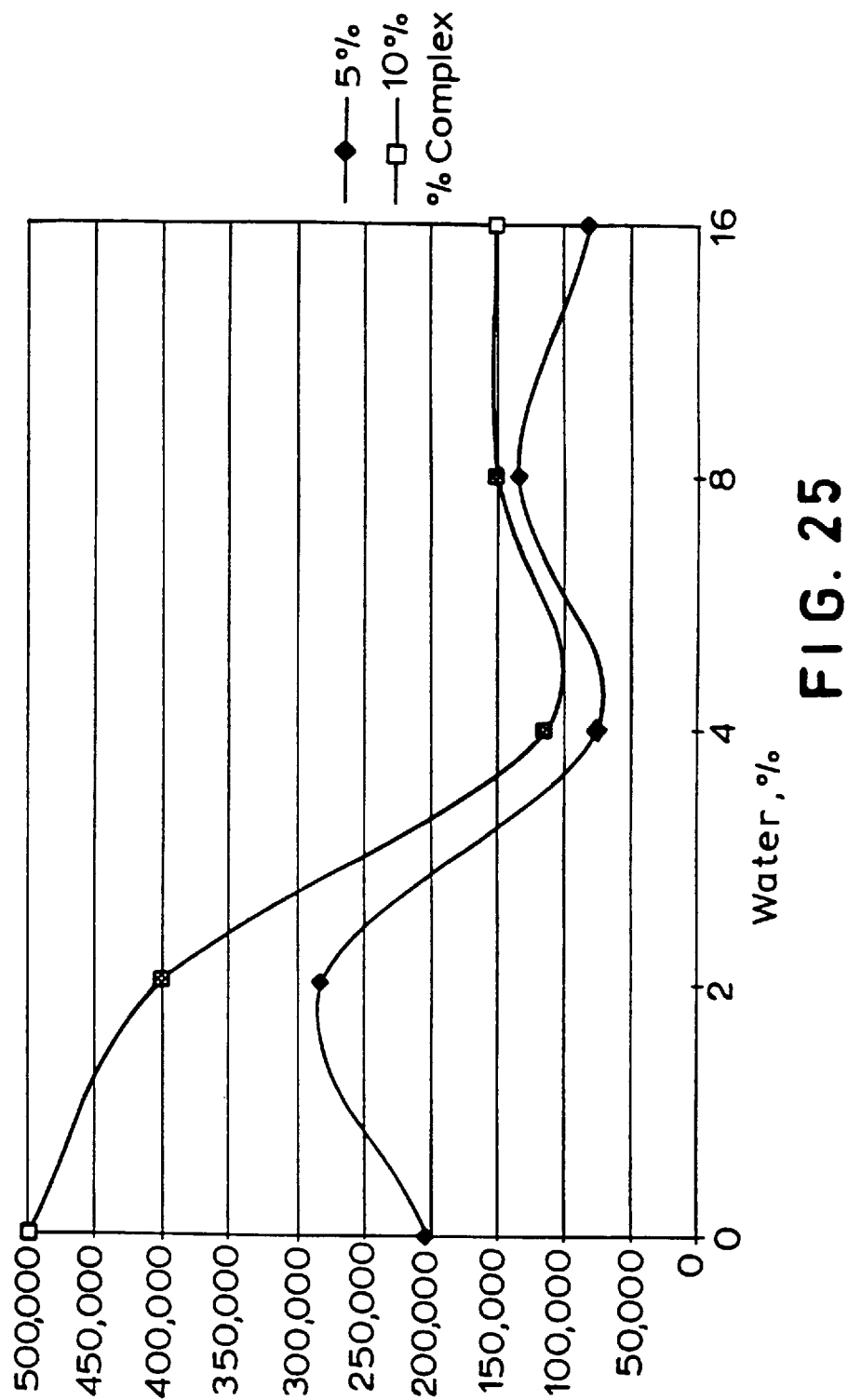
FIG. 25 is a graph of composition viscosity at 24° C. of compositions of varied percentages of water and glycerol at 0–16% by weight water and 84–100% by weight glycerol at 5% by weight and 10% by weight loadings of a complex of Na bentonite clay:PVP (4:1 clay:PVP weight ratio) showing the change in viscosity at various water percentages ($H_2O$ plus glycerol=100%) at various clay:PVP complex loadings.

FIG. 16 shows an x-ray diffraction pattern from a melted (280° C.) blend of 50% by weight polycarbonate and 50% by weight sodium bentonite (containing about 8% by weight moisture). As shown, no characteristic smectite d(001) peak appears at about 12.4 Å for the melted blend, indicating that the clay was intercalated with the polycarbonate, and the platelets were exfoliated.

As shown in the graphs of FIGS. 9–16, when the mechanical blends were heated to the polymer melt temperature, and preferably at least about 40°–50° C. above the polymer melt temperature for faster reaction (intercalation, exfoliation), the polymer melt was intercalated between the bentonite clay platelets. It should be noted, also, that exfoliation did not occur unless the bentonite clay included water in an amount of at least about 5% by weight, based on the dry weight of the clay, preferably about 10% to about 15% water. The water can be included in the clay as received, or can be added to the clay prior to or during polymer contact.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. The details of the structure may be varied substantially without departing from the spirit of the invention, and the exclusive use of all modifications which come within the scope of the appended claims is reserved.

What is claimed is:

1. A method of increasing the viscosity of an organic liquid by combining said organic liquid with an intercalate complex of a phyllosilicate and polymer comprising:

contacting the phyllosilicate, having a water content of at least about 4% by weight, with an intercalant polymer, without an onium ion or silane coupling agent, to form an intercalating composition having a weight ratio of intercalant polymer to phyllosilicate of at least 1:20, to form an intercalate, wherein intercalation of said polymer between said adjacent phyllosilicate platelets of said intercalate is sufficient to space said adjacent phyllosilicate platelets a distance of at least about 5 Å; and combining said intercalate with said organic liquid.

2. The method of claim 1, wherein said intercalating composition includes a water intercalating carrier comprising about 4% to about 5000% by weight water, capable of dissolving said polymer, based on the dry weight of said phyllosilicate.

3. A method in accordance with claim 1, wherein the weight ratio of intercalant polymer to phyllosilicate material in the intercalating composition is in the range of 1:20 to 1:3.

4. A method in accordance with claim 3, wherein the weight ratio of polymer to layered material complexed between adjacent spaced layers of the layered silicate material is from about 20 grams of polymer per 100 grams of layered silicate material to about 60 grams of polymer per 100 grams of layered silicate material.

5. A method in accordance with claim 3, wherein the weight ratio of intercalant polymer to layered material in the intercalating composition is in the range of 1:20 to 14:20.

6. A method in accordance with claim 1, wherein the weight ratio of polymer to phyllosilicate material complexed between adjacent spaced layers of the phyllosilicate is from about 8 grams of polymer per 100 grams of phyllosilicate to about 90 grams of polymer per 100 grams of phyllosilicate.

7. A method in accordance with claim 6, wherein the weight ratio of polymer to phyllosilicate complexed between adjacent spaced layers of the phyllosilicate is from about 16 grams of polymer per 100 grams of phyllosilicate to about 90 grams of polymer per 100 grams of phyllosilicate.

8. A method in accordance with claim 7, wherein the weight ratio of polymer to phyllosilicate complexed between adjacent spaced layers of the phyllosilicate is from about 16 grams of polymer per 100 grams of phyllosilicate to about 80 grams of polymer per 100 grams of phyllosilicate.

9. A method in accordance with claim 8, wherein the weight ratio of polymer to phyllosilicate complexed between adjacent spaced layers of the phyllosilicate is from about 20 grams of polymer per 100 grams of phyllosilicate to about 60 grams of polymer per 100 grams of phyllosilicate.

10. A method in accordance with claim 1, wherein the weight ratio of intercalant polymer to phyllosilicate in the intercalating composition is in the range of 1:20 to 14:20.

* * * * *

UNITED STATES PATENT AND TRADEMARK OFFICE
CERTIFICATE OF CORRECTION

PATENT NO.   : 5,877,248
DATED        : March 2, 1999
INVENTOR(S)  : Beall et al.

Page 1 of 1

It is certified that error appears in the above-identified patent and that said Letters Patent is hereby corrected as shown below:

Column 5,
Line 33, delete "is".

Column 6,
Line 21, replace "5" with -- 5% --.

Column 8,
Line 26, replace "100%" with -- ≈100% --.

Column 9,
Line 13, replace "100%" with -- ≈100% -- and delete ".t".

Column 19,
Line 42, replace "hydroxyguinoline" with -- hydroxyquinoline --.

Column 22,
Line 30, replace "%0" with -- to --.

Column 27,
Line 56, replace "%he" with -- the --.

Signed and Sealed this

Twenty-first Day of May, 2002

Attest:

JAMES E. ROGAN
Attesting Officer   Director of the United States Patent and Trademark Office